United States Patent
Grey et al.

(10) Patent No.: US 9,282,878 B2
(45) Date of Patent: Mar. 15, 2016

(54) CYCLO OLEFIN POLYMER AND COPOLYMER MEDICAL DEVICES

(75) Inventors: Thomas L. Grey, San Marcos, CA (US); Fernando Erismann, New York, NY (US); Alex Vayser, Mission Viejo, CA (US)

(73) Assignee: INVUITY, INC., San Francisco, CA (US)

( * ) Notice: Subject to any disclaimer, the term of this patent is extended or adjusted under 35 U.S.C. 154(b) by 311 days.

(21) Appl. No.: 13/026,910

(22) Filed: Feb. 14, 2011

(65) Prior Publication Data

US 2012/0041268 A1 Feb. 16, 2012

Related U.S. Application Data

(63) Continuation-in-part of application No. 12/191,164, filed on Aug. 13, 2008, now Pat. No. 8,317,693.

(51) Int. Cl.
| | | |
|---|---|---|
| A61B 1/32 | (2006.01) |
| A61B 1/00 | (2006.01) |
| A61B 1/06 | (2006.01) |
| A61B 1/07 | (2006.01) |
| A61B 1/267 | (2006.01) |
| A61B 1/303 | (2006.01) |
| A61B 17/02 | (2006.01) |
| A61B 17/34 | (2006.01) |

(Continued)

(52) U.S. Cl.
CPC ............ *A61B 1/00105* (2013.01); *A61B 1/0623* (2013.01); *A61B 1/07* (2013.01); *A61B 1/267* (2013.01); *A61B 1/303* (2013.01); *A61B 1/32* (2013.01); *A61B 17/02* (2013.01); *A61B 17/0206* (2013.01); *A61B 17/0293* (2013.01); *A61B 17/3421* (2013.01); *A61B 19/5202* (2013.01); *A61L 29/041* (2013.01); *A61B 2017/00734* (2013.01); *A61B 2019/5206* (2013.01)

(58) Field of Classification Search
USPC ............ 385/14–15, 114, 123–128, 141–146; 600/184–249; 264/1.24
See application file for complete search history.

(56) References Cited

U.S. PATENT DOCUMENTS

| | | |
|---|---|---|
| 3,638,644 A | 2/1972 | Reick |
| 3,641,332 A | 2/1972 | Reick et al. |

(Continued)

FOREIGN PATENT DOCUMENTS

| | | |
|---|---|---|
| CN | 1861656 A | 11/2006 |
| CN | 101081889 A | 12/2007 |

(Continued)

OTHER PUBLICATIONS

International search report and written opinion dated Mar. 30, 2010 for PCT/US2009/053438.

(Continued)

*Primary Examiner* — Anu Ramana
*Assistant Examiner* — Jessica Weiss
(74) *Attorney, Agent, or Firm* — Wilson Sonsini Goodrich & Rosati

(57) ABSTRACT

An illuminated medical system comprises a medical instrument and a light transmitting waveguide. The waveguide projects lights from a distal portion of the waveguide toward a target area. The waveguide is formed primarily of a cyclic olefin copolymer or a cyclic olefin polymer.

39 Claims, 24 Drawing Sheets

(51) Int. Cl.
*A61B 19/00* (2006.01)
*A61L 29/04* (2006.01)
*A61B 17/00* (2006.01)

(56) References Cited

U.S. PATENT DOCUMENTS

| | | | |
|---|---|---|---|
| 3,890,960 | A | 6/1975 | Wunsch et al. |
| 4,226,228 | A | 10/1980 | Shin et al. |
| 4,562,832 | A | 1/1986 | Wilder et al. |
| 4,592,344 | A | 6/1986 | Scheer |
| 4,597,030 | A | 6/1986 | Brody et al. |
| 4,605,990 | A | 8/1986 | Wilder et al. |
| 4,643,172 | A | 2/1987 | Taff et al. |
| 4,697,578 | A | 10/1987 | Burgin |
| 4,807,599 | A | 2/1989 | Robinson et al. |
| 4,842,356 | A | 6/1989 | Mori |
| 4,961,617 | A | 10/1990 | Shahidi et al. |
| 5,035,232 | A | 7/1991 | Lutze et al. |
| 5,353,786 | A | 10/1994 | Wilk |
| 5,995,696 | A | 11/1999 | Miyagi et al. |
| 6,139,493 | A * | 10/2000 | Koros et al. .......... 600/215 |
| 6,185,356 | B1 | 2/2001 | Parker et al. |
| 6,482,153 | B1 | 11/2002 | Hipps et al. |
| 6,504,985 | B2 | 1/2003 | Parker et al. |
| 6,554,768 | B1 | 4/2003 | Leonard |
| 6,824,286 | B2 | 11/2004 | Sugiyama |
| 7,231,122 | B2 * | 6/2007 | Weisberg et al. ........... 385/123 |
| 7,306,559 | B2 * | 12/2007 | Williams ............... 600/245 |
| 7,711,221 | B2 | 5/2010 | Burgi et al. |
| 8,267,855 | B2 | 9/2012 | Barker |
| 8,280,212 | B2 * | 10/2012 | Goell et al. ........... 385/123 |
| 8,864,662 | B2 | 10/2014 | Grey et al. |
| 2005/0165283 | A1 * | 7/2005 | Hestad et al. ........ 600/212 |
| 2005/0203341 | A1 * | 9/2005 | Welker et al. ........ 600/130 |
| 2005/0259933 | A1 * | 11/2005 | Temelkuran et al. ...... 385/123 |
| 2005/0279354 | A1 | 12/2005 | Deutsch |
| 2006/0256575 | A1 | 11/2006 | Vayser |
| 2007/0106175 | A1 | 5/2007 | Uchiyama et al. |
| 2007/0189701 | A1 | 8/2007 | Chakmakjian et al. |
| 2007/0239149 | A1 | 10/2007 | Lieponis |
| 2008/0125556 | A1 | 5/2008 | Ohkita et al. |
| 2008/0147018 | A1 | 6/2008 | Squilla |
| 2009/0105546 | A1 | 4/2009 | Hestad et al. |
| 2009/0251776 | A1 * | 10/2009 | Ouderkirk et al. ............ 359/497 |
| 2010/0041955 | A1 | 2/2010 | Grey et al. |
| 2010/0267170 | A1 | 10/2010 | Swanson et al. |

FOREIGN PATENT DOCUMENTS

| | | |
|---|---|---|
| EP | 0101781 A1 | 3/1984 |
| GB | 2078526 A | 1/1982 |
| GB | 2133694 A | 8/1984 |
| GB | 2321972 A | 8/1998 |
| JP | H 04336059 A | 11/1992 |
| JP | 2004069879 A | 3/2004 |
| JP | 2005353406 A | 12/2005 |
| JP | 2008112301 A | 5/2008 |
| WO | WO2007084641 A2 | 7/2007 |

OTHER PUBLICATIONS

International search report and written opinion dated Jun. 19, 2012 for PCT/US2012/024895.
Office action dated Feb. 8, 2012 for U.S. Appl. No. 12/191,164.
Office action dated Jul. 27, 2011 for U.S. Appl. No. 12/191,164.
U.S. Appl. No. 13/660,679, filed Oct. 25, 2012, Grey et al.
Office action dated Nov. 27, 2013 for U.S. Appl. No. 13/660,679.
European search report and opinion dated Dec. 12, 2013 for EP Application No. 09807182.2.
Notice of allowance dated Jun. 11, 2014 for U.S. Appl. No. 13/660,679.
Notice of allowance dated Jul. 19, 2012 for U.S. Appl. No. 12/191,164.

* cited by examiner

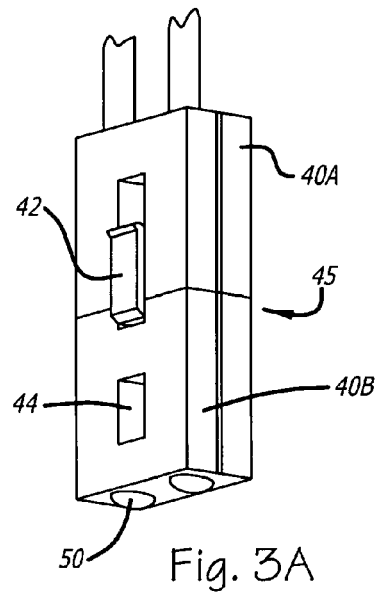
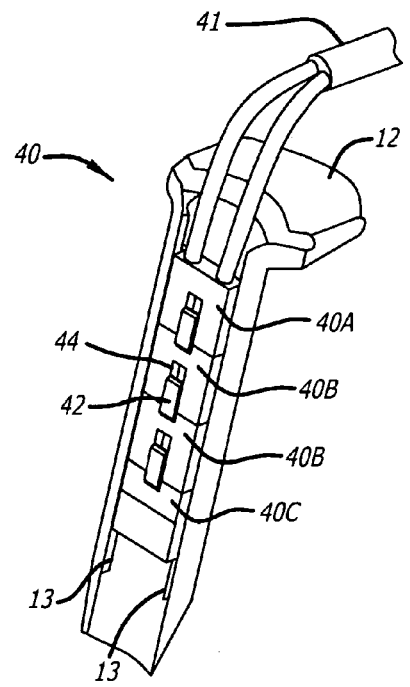
Fig. 3
Fig. 3A
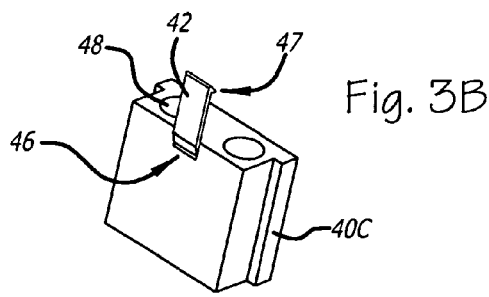
Fig. 3B
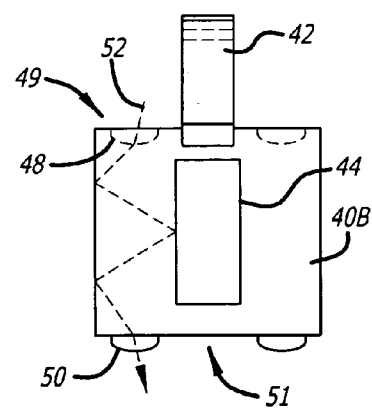
Fig. 3C

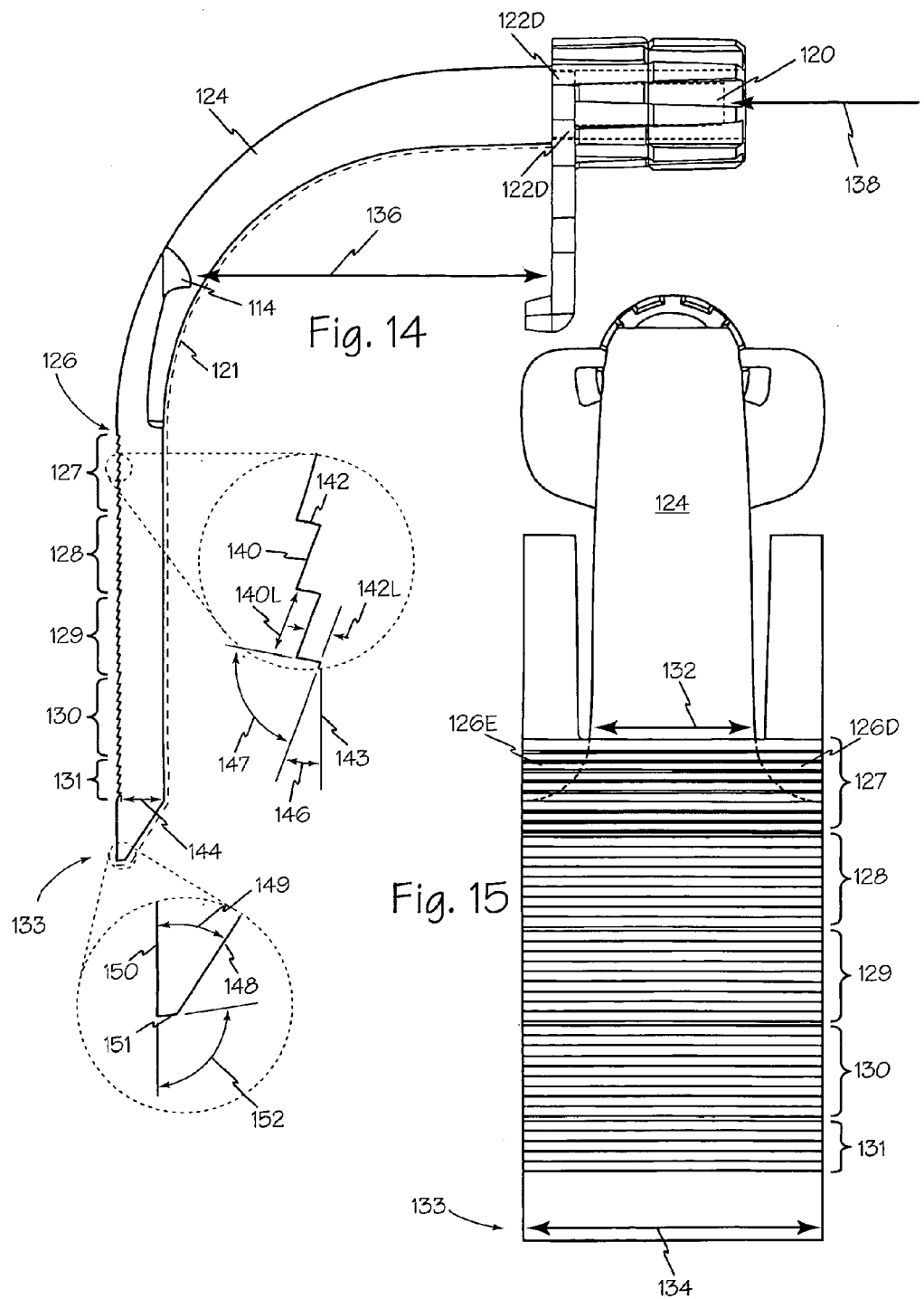

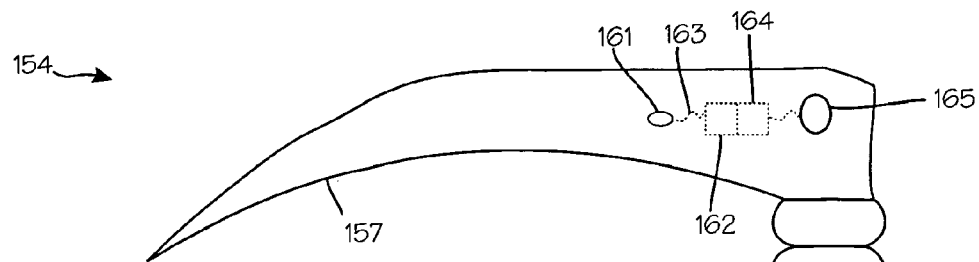
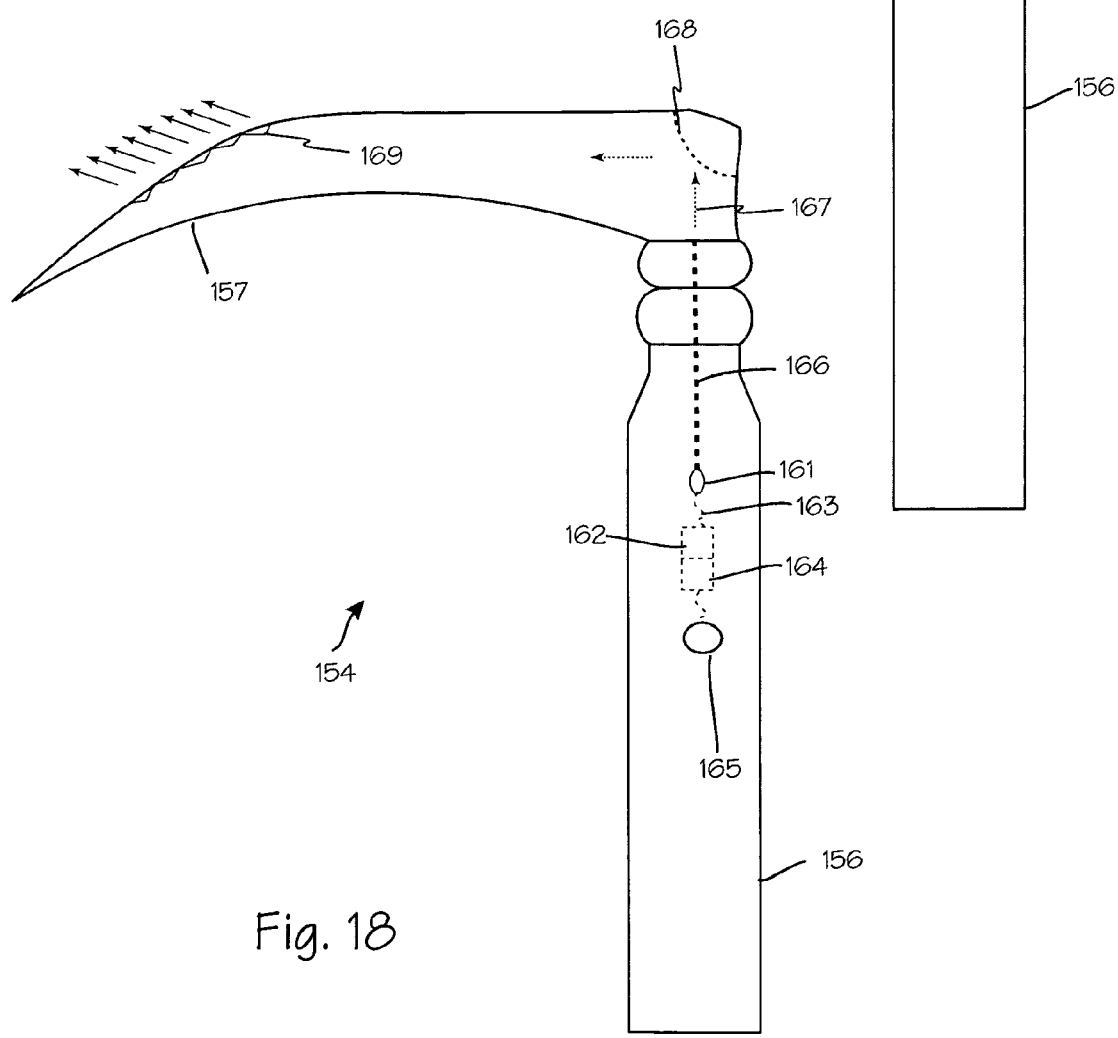

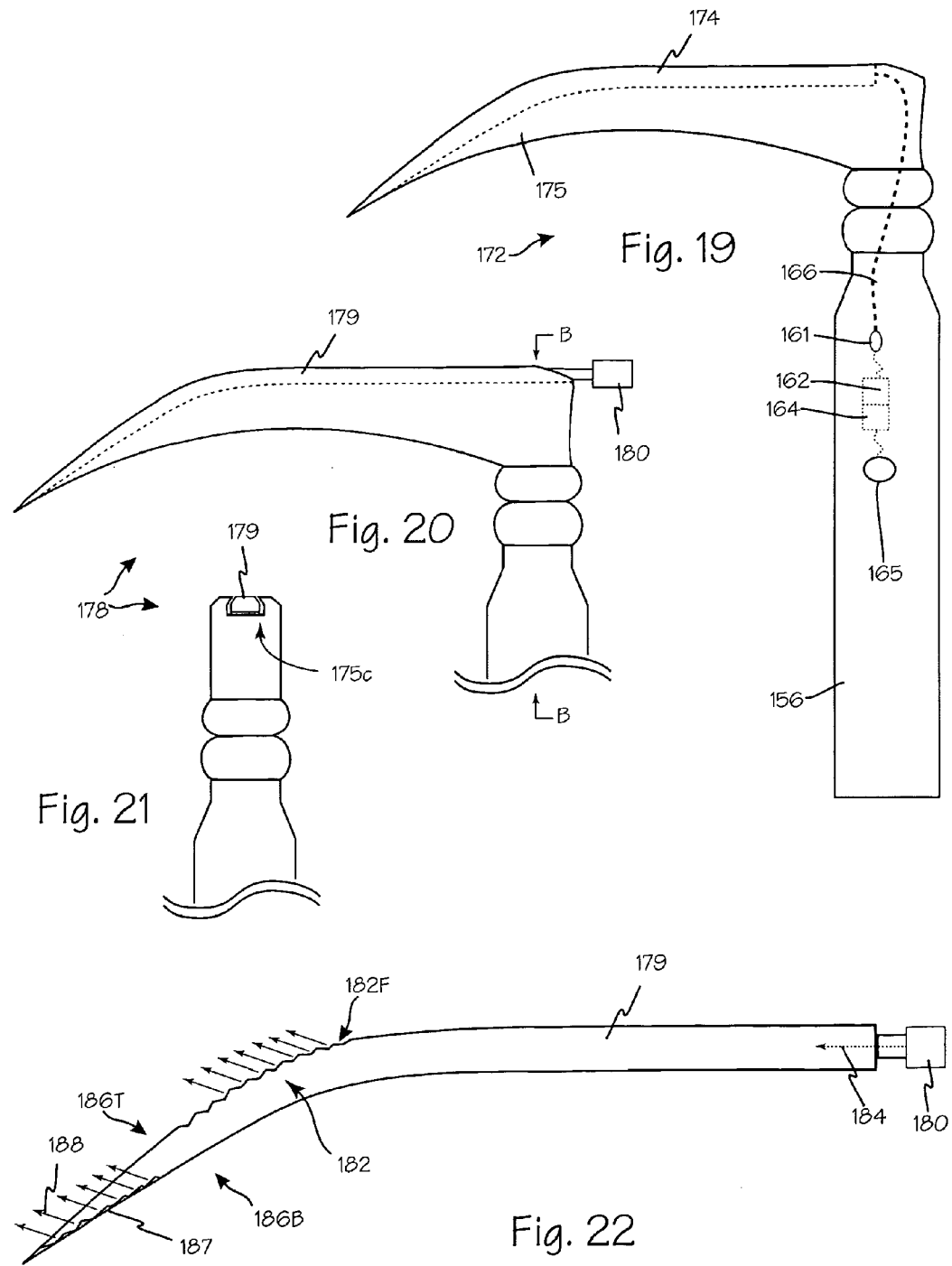

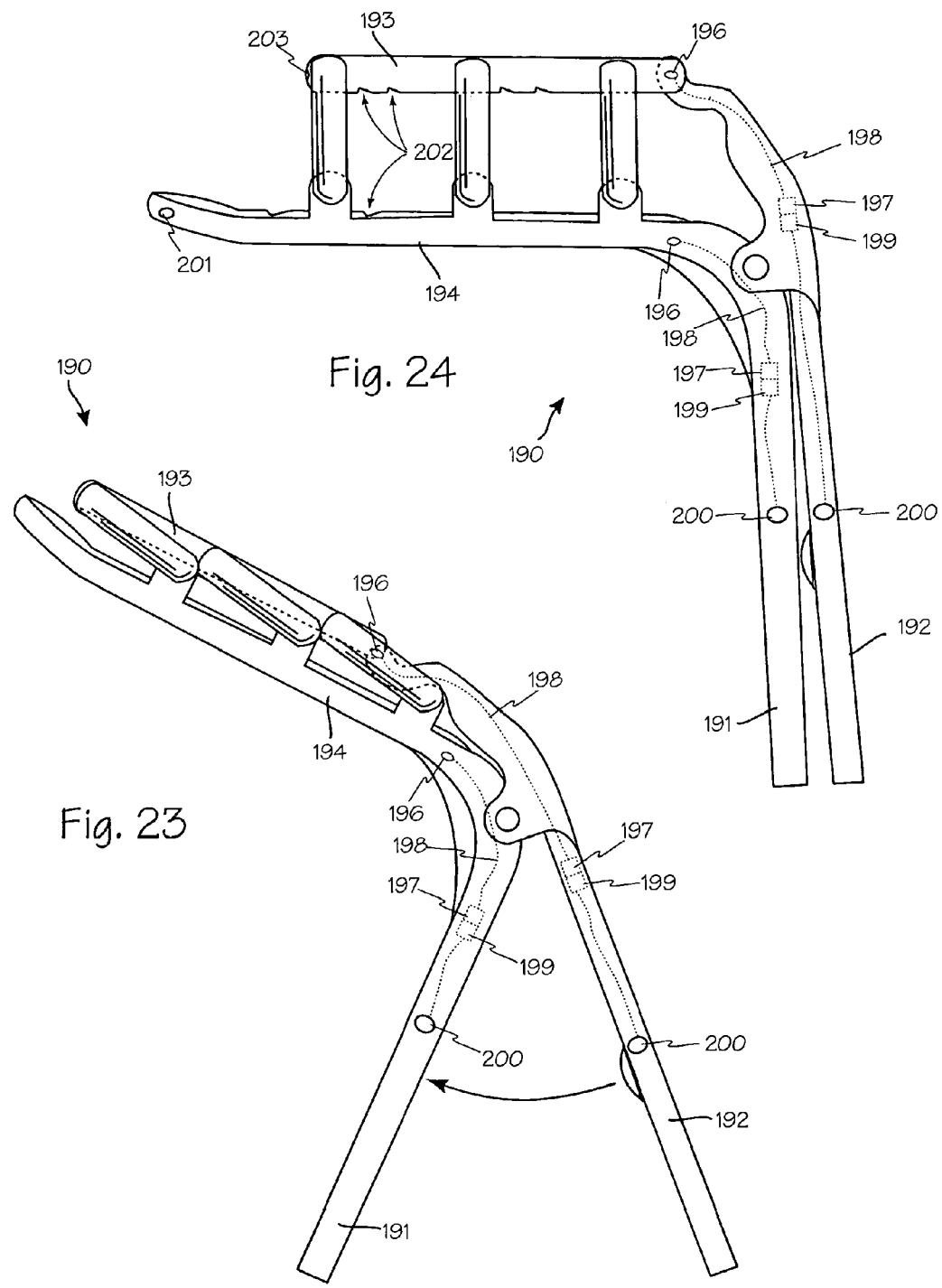

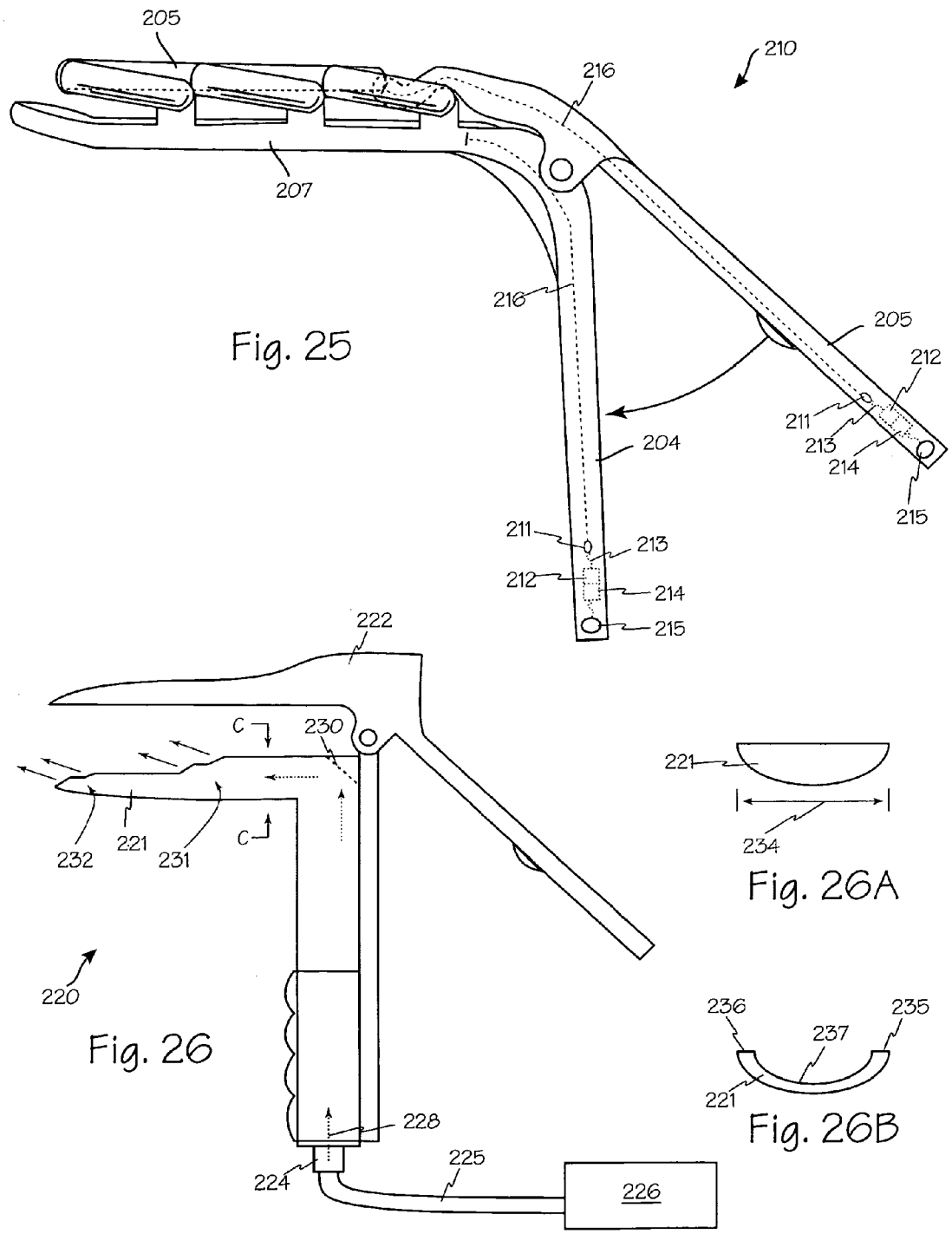

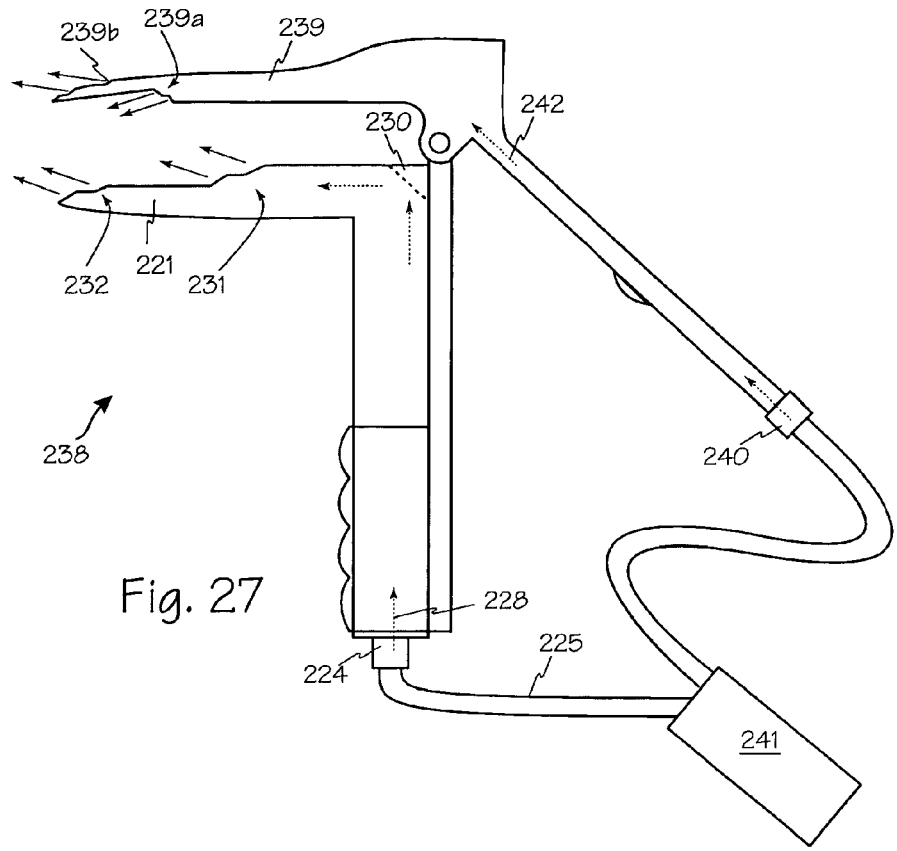
Fig. 27
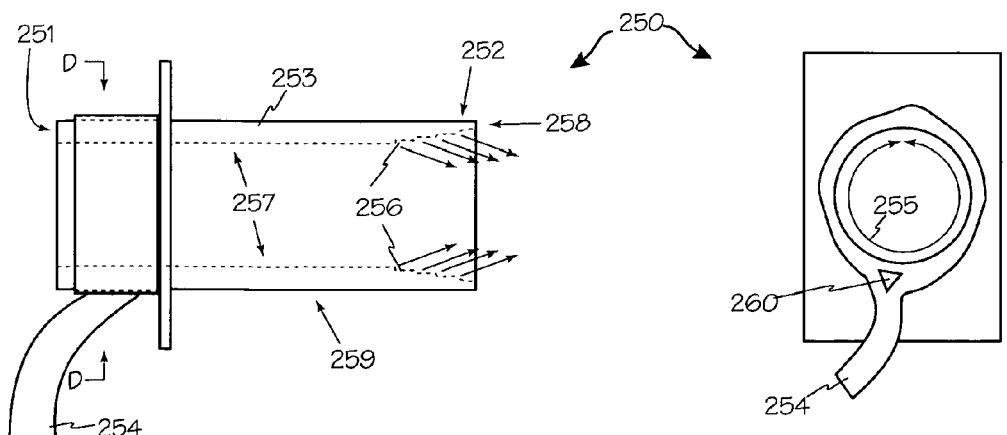
Fig. 28
Fig. 29

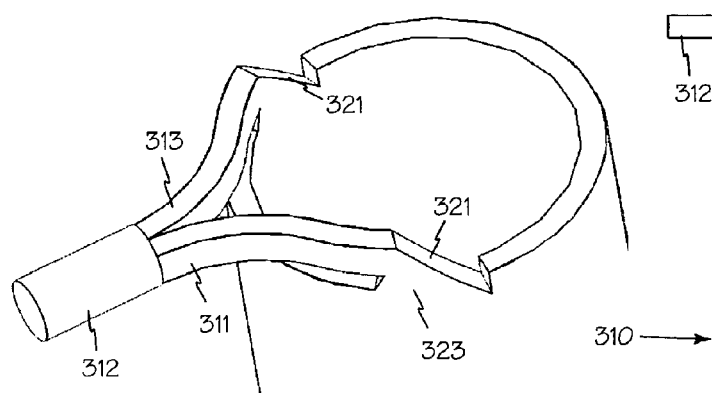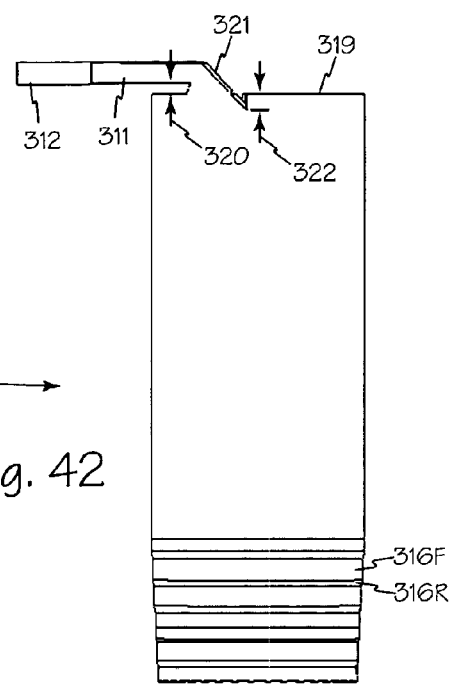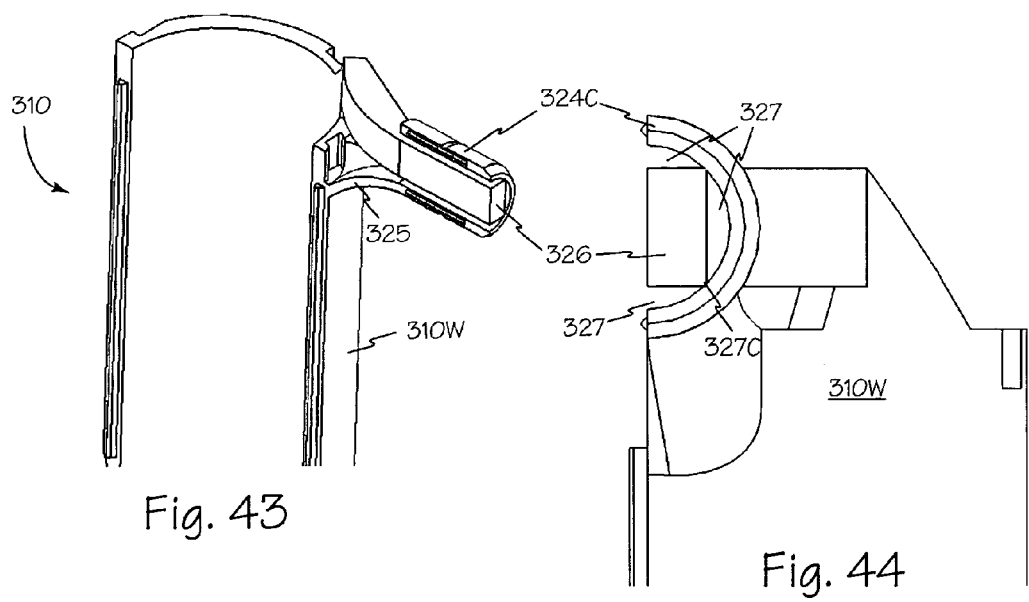
Fig. 41
Fig. 42
Fig. 43
Fig. 44

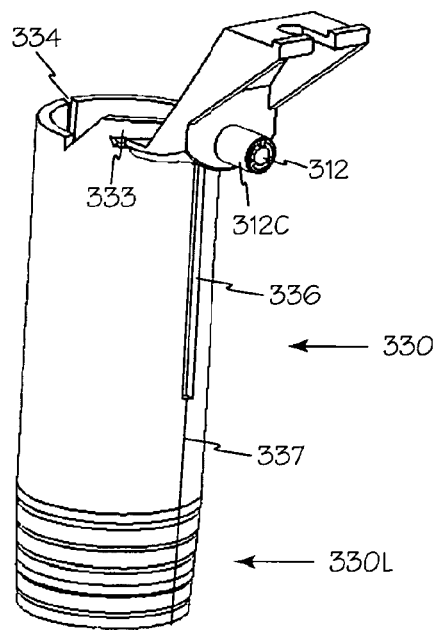
Fig. 45
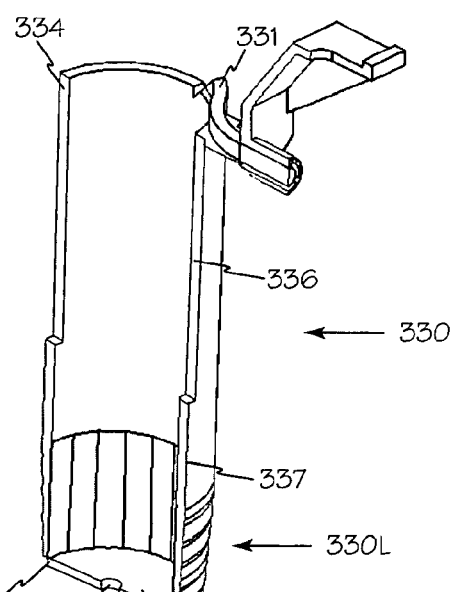
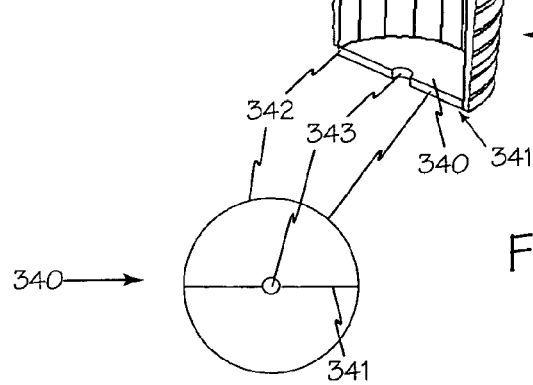
Fig. 46

CYCLO OLEFIN POLYMER AND COPOLYMER MEDICAL DEVICES

CROSS-REFERENCES TO RELATED APPLICATIONS

This application is a continuation-in-part of U.S. patent application Ser. No. 12/191,164, filed Aug. 13, 2008, the entire contents of which are incorporated herein by reference.

BACKGROUND OF THE INVENTION

1. Field of the Invention

The inventions described below relate generally to the field of in vivo surgical field illumination during medical and surgical procedures.

2. Background of the Invention

Illumination of body cavities for diagnosis and or therapy has been limited by overhead illumination. High intensity incandescent lighting has been developed and has received limited acceptance as well as semiconductor and laser lighting, however these light sources have a heat and weight penalty associated with their use. Excessive heat can cause unwanted coagulation of blood, as well as unnecessarily heating of a patient's body. Additionally, heat buildup can cause various components fabricated from some polymers to exceed their glass transition temperature and deform. Heat buildup may also cause optical properties of various components to be compromised. Weight of some illumination systems makes them uncomfortable for an operator, especially during a lengthy procedure. Conventional light sources rely on fiber optic and similar waveguide materials to conduct light to a body cavity. Conventional waveguide materials that are suggested for medical use suffer from some of the unstable transmission characteristics under extended use described above, and their transmission characteristics may also change when sterilized using conventional techniques (e.g. autoclave, EtO, gamma or e-beam irradiation). Additionally, precision optical polymers have limited mechanical properties which limits their application in medical/surgical situations.

Examples of conventional polymers that have traditionally been used with some success in surgical illumination systems include acrylics such as polymethylmethacrylate (PMMA) and polycarbonates (PC) such as Lexan®. Polycarbonate is desirable since it may be fabricated into various configurations which may be slightly bent without shattering. While polycarbonate has good mechanical strength and manufacturability, its optical properties are not optimal. For example, polycarbonate has a low light transmission efficiency, and therefore is not ideal for transmitting light, especially along a long pathway. Acrylic has also been used with some success in surgical illumination systems. It is more efficient at transmitting light than polycarbonate, is easy to process (e.g. may be injection molded), but acrylic is also brittle and can shatter. Also, acrylic has a relatively low glass transition temperature, and thus acrylic components do not tolerate heat buildup well, especially in medical illumination systems where heat is generated during use. Acrylic also absorbs moisture and this changes the refractive index of the material which can alter its performance. Therefore, it would be desirable to provide a material that is better suited for medical illumination systems and that has at least some of the desirable mechanical and optical properties of acrylic or polycarbonate while minimizing the less desired properties. For example, such materials would preferably have equivalent or better light transmission efficiency than acrylic, a higher glass transition temperature relative to acrylic, be easy to process like acrylic or polycarbonate, have better resistance to moisture absorption than acrylic, and be bendable without shattering like polycarbonate. Moreover, the material used must also be able to withstand terminal sterilization without compromising optical properties. Many polymers discolor when irradiated or can deform due to exposure to heat during sterilization. It would therefore also be advantageous to provide a material that can be terminally sterilized without damage. Also, any materials used in a medical application must also be biocompatible. At least some of these challenges will be addressed by the exemplary embodiments disclosed below.

BRIEF SUMMARY OF THE INVENTION

The devices described below provide for surgical retraction or illumination, or both, with devices made primarily of an amorphous polyolefin, cyclo olefin copolymer (COC) or cyclo olefin polymer (COP). While many of the embodiments described below preferably use COP, one of skill in the art will appreciate that COC may also be used.

Preferably, a retractor formed primarily of cyclo olefin polymer is used as the illumination device. A surgical illumination system formed of cyclo olefin polymer may include a generally cylindrical light waveguide having a bore sized to accommodate one or more surgical instruments, an illumination source, an illumination conduit for conducting illumination energy from the illumination source, and an adapter ring for engaging the illumination conduit and coupling illumination energy from the illumination conduit to the light waveguide. The adapter ring may permit relative movement between the illumination conduit and the light waveguide.

The new illumination system may also include an illumination source, a generally cylindrical light waveguide formed of cyclo olefin polymer having a distal end and a proximal end, and a bore sized to accommodate one or more instruments or tools extending from the proximal end through the distal end. The waveguide conducts light from the proximal end to the distal end and projects the light from the distal end. The illumination conduit conducts light from the light source to the proximal end of the light waveguide.

A COP illumination system may also include any suitable retractor system such as McCulloch retractor, and includes a channel in the retractor blade to accommodate a COP illuminator. In this system, the COP illuminator is also formed to have an air gap surrounding any active portion of the illuminator from the light input to the light output portion. The illuminator has active portions in which light passes and inactive or dead zones in which light does not pass as a result of the configuration and orientation of the input, output and surfaces of the illuminator. The dead zones may include elements to allow the illuminator to securely engage the retractor.

The medical retractor system as described below includes a cannula, retractor or retractor blade having a cyclo olefin polymer element extending from the proximal end thereof to the distal end thereof, a light source operably coupled to the proximal end of the cyclo olefin polymer element, and at least one light extracting element near the distal end of the cyclo olefin polymer element.

A COP blade insert illumination system includes one or more illumination elements composed of cyclo olefin polymer. The COP illumination elements operate as a waveguide and may incorporate optical components such as, for example, symmetric or asymmetric facets, lenses, gratings, prisms and or diffusers to operate as precision optics for customized delivery of the light energy. The illumination elements may be modular, allowing components to be mixed and matched for different sizes of blade retractors, or may be a single integrated unit. Each module may also have different performance characteristics such as a diffuse light output or a focused light output allowing users to mix and match optical performance as well.

Any dissecting tools and/or retractors for small surgical sites such as the hand or foot may be formed of COP with a light input at the proximal end to enable the distal end to illuminate the surgical site. One or more structural elements such as wire may be co-molded into a COP tool for increased mechanical strength. A suitable COP compound is produced by Zeon Chemicals L.P. under the trademark Zeonor® and Zeonex®. These two polymers have at least some of the mechanical characteristics and at least some of the optical stability and characteristics for use in an illuminated medical system.

In one aspect of the present invention, an illuminated medical system comprises a medical instrument and a light transmitting waveguide. The waveguide has a proximal region and a distal region, and is coupled to the medical instrument. The waveguide is configured to conduct light from the proximal region to the distal region thereof, and the waveguide projects the light from an extraction area preferably near the distal portion of the waveguide toward a target area. The waveguide is formed primarily of a cyclic olefin copolymer or a cyclic olefin polymer.

The medical instrument may comprise one of a surgical retractor, a laryngoscope, a speculum, or an anoscope. Other medical instruments are also contemplated for use. The waveguide may be adjustably positionable relative to the medical instrument thereby allowing adjustment of the projected light onto the target area. The waveguide may further comprise one or more output optical structures disposed adjacent the distal portion thereof. The output optical structures may be configured to direct the light from the distal portion of the waveguide to the target area as well as the surface of the waveguide. The output optical structures may comprise one or more facets. The waveguide may comprise a tubular body, an elongate blade, or a half tubular body. The system may further comprise an illumination source, an illumination conduit, and an optical coupling. The illumination source may provide the light. The illumination conduit may be optically coupled with the illumination source and the waveguide. The illumination conduct may be configured to conduct light from the illumination source to the waveguide. The optical coupling may be coupled to the waveguide and the illumination conduit. The optical coupling may be configured to optically couple the illumination conduit with the waveguide so that the light may pass therebetween. The optical coupling also may be used to releasably hold the illumination conduit and the waveguide together.

In still another aspect of the present invention, an illuminated medical system comprises a medical instrument and a light transmitting illuminator. The illuminator has a proximal region and a distal region, and is coupled to the medical instrument. The illuminator is configured to conduct light from the proximal region to the distal region thereof, and the illuminator comprises a light input portion, a light conducting portion, and a light output portion. The light output portion projects the light from the distal portion of the illuminator towards a target area, and the light conducting portion is formed primarily of a cyclic olefin copolymer or a cyclic olefin polymer.

The light output portion may be adjustably positionable relative to the medical instrument thereby allowing adjustment of the projected light onto the target area. The light output portion may comprise one or more output optical structures disposed adjacent the distal end thereof. The output optical structures may be configured to direct the light from the light output portion to the target area. The output optical structures may comprise one or more facets. The light conducting portion may comprise a tubular body, an elongate blade, or a half tubular body. The system may further comprise an illumination source that provides the light, and an illumination conduit. The illumination conduit may be optically coupled with the light input portion and the illumination source, and the conduit may be configured to conduct light from the illumination source to the light input portion. An index matching material such as a liquid or gel may be used to help optically couple the components together.

In yet another aspect of the present invention, a method for illuminating a medical work space comprises providing a medical instrument coupled to a light transmitting waveguide, and advancing the medical instrument and the waveguide toward the work space. The method also comprises illuminating the work space with light from the waveguide. The light passes from a proximal portion of the waveguide to a distal portion of the waveguide. The waveguide is formed primarily of a cyclic olefin copolymer or a cyclic olefin polymer.

The medical instrument may comprise one of a surgical retractor, a laryngoscope, a speculum, or an anoscope. Advancing the medical instrument and the waveguide may further comprise positioning the medical instrument in a patient and retracting tissue with the medical instrument. Advancing the medical instrument and the waveguide may comprise positioning the medical instrument and the waveguide in a body orifice or into an incision. The waveguide may comprise a tubular body having a central channel, and advancing the medical instrument may comprise positioning the medical instrument through the central channel. Illuminating may comprise adjusting the waveguide position relative to the medical instrument, thereby adjusting illumination of the work space. Illuminating may comprise optically coupling the waveguide with an illumination source.

In any of the embodiments disclosed herein, the waveguide or the light conducting portion of the illuminator may have a specific gravity less than that of polycarbonate or acrylic. The water absorption rate of the waveguide or the light conducting portion of the illuminator may be less than that of polycarbonate or acrylic. Therefore, the water absorption rate is preferably less than 0.01%. The light transmission efficiency of the waveguide or light conducting portion of the illuminator may be greater than that of polycarbonate or greater than or equal to that of acrylic. Thus, the light transmission efficiency is preferably greater than 90% and more preferably greater than 92%. The waveguide or the light conducting portion of the illuminator may have a refractive index greater than acrylic, and the glass transition temperature thereof may be greater than that of polycarbonate or acrylic. Thus, the refractive index is preferably greater than 1.49, and the glass transition temperature is greater than or equal to 105° C. The waveguide or illuminator is preferably biocompatible.

These and other embodiments are described in further detail in the following description related to the appended drawing figures.

BRIEF DESCRIPTION OF THE DRAWINGS

FIG. 3 is a perspective view of another COP blade insert illuminator.

FIG. 3A is a close perspective view of the light output section of the COP blade illuminator of FIG. 3.

FIG. 3B is a close perspective view of a conduit section of the COP blade illuminator of FIG. 3.

FIG. 3C is a front view of a light ray path for a light conduit section of the COP blade illuminator of FIG. 3.

FIG. 12A is an exploded view of the input collar and the illumination blade input.

FIG. 14 is a side view of the COP illumination blade of FIG. 12.

FIG. 15 is a front view of the COP illumination blade of FIG. 12.

FIG. 17 is a side view of a COP laryngoscope illumination system with an illumination source in the blade.

FIG. 18 is a side view of a COP laryngoscope illumination system with an illumination source in the handle.

FIG. 19 is a side view of an alternate COP laryngoscope illuminator according to the present disclosure.

FIG. 20 is a side view of a metal blade laryngoscope including a COP illuminator waveguide engaging the blade.

FIG. 21 is a cross section of the laryngoscope with COP illuminator waveguide of FIG. 20 taken along B-B.

FIG. 22 is a side view of a COP laryngoscope cavity illuminator waveguide.

FIG. 23 is a side view of a COP speculum illumination system.

FIG. 24 is a side view of the COP cavity illumination system of FIG. 23 with the handles closed.

FIG. 25 is a side view of an alternate COP cavity illumination system with the illumination source in the handle.

FIG. 26 is a side view of another alternate COP cavity illumination system.

FIG. 26A is a cutaway view of the COP blade of cavity illumination system of FIG. 26 taken along C-C.

FIG. 26B is a cutaway view of an alternate COP blade of cavity illumination system of FIG. 26 taken along C-C.

FIG. 27 is a side view of still another alternate COP cavity illumination system.

FIG. 28 is a top view of yet another COP cavity illumination system according to the present disclosure.

FIG. 29 is a cutaway view of the COP cavity illumination system of FIG. 28 taken along D-D.

FIG. 41 is a perspective view of the COP optical waveguide of FIG. 39 with the clamp assembly removed for clarity.

FIG. 42 is a side view of the COP optical waveguide of FIG. 41.

FIG. 43 is a cutaway perspective view of a COP optical waveguide with the clamp assembly removed for clarity.

FIG. 44 is a close up front view of the input connector of FIG. 43.

FIG. 45 is a perspective view of a separable COP waveguide.

FIG. 46 is a cutaway view of the COP optical waveguide of FIG. 45.

DETAILED DESCRIPTION OF THE INVENTION

Figures 1, 1A, 1B:
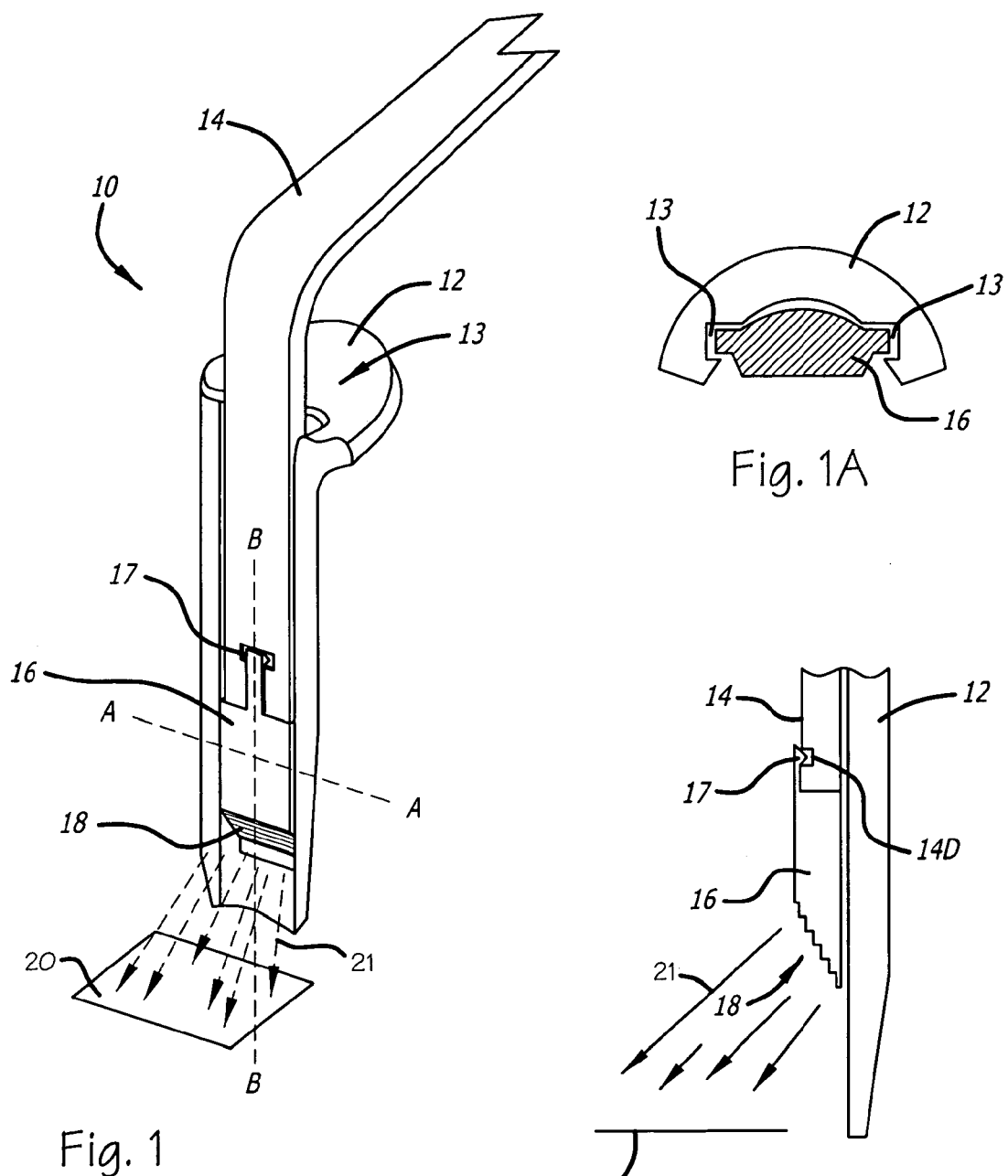
FIG. 1 is a perspective view of a COP blade insert illuminator.
FIG. 1A is a cross-section of the COP blade insert illuminator of FIG. 1 taken along A-A.
FIG. 1B is a cross-section of the COP blade insert illuminator of FIG. 1 taken along B-B.

Cyclic olefin copolymer (COC) and cyclic olefin polymer (COP) are a relatively new class of optical polymers that have glass-like clarity, and therefore are promising materials for optical components used in illuminated medical systems. COC is an amorphous polymer produced by chain copolymerization of cyclic monomers such as 8,9,10-trinorborn-2-ene (norbornene) or 1,2,3,4,4a,5,8,8a-octahydro-1,4:5,8-dimethanonaphthalene (tetracyclododecene) with ethane, TOPAS Advanced Polymer's TOPAS, Mitsui Chemical's APEL, or by ring-opening metathesis polymerization of various cyclic monomers followed by hydrogenation (e.g. Japan Synthetic Rubber's ARTON, Zeon Chemical's Zeonex and Zeonor). These later materials using a single type of monomer are more properly referred to as cyclic olefin polymers (COP).

COC and COP have transparency similar to glass in its natural form. Therefore they may be used in optical components such as a waveguide, illuminator, or any of the components in the illuminated medical system, instead of acrylic or polycarbonate. COC and COP also have a high moisture barrier for a clear polymer and a low absorption rate. They are recognized to be a high purity product with low extractables and are halogen free. While material properties will vary due to monomer content, glass transition temperature can exceed 150° C. Moreover, while COC and COP may be attacked by non-polar solvents such as toluene, they nevertheless provide good chemical resistance to many other solvents.

COC and COP may be extruded, coextruded, vacuum formed, injection molded, and can be terminally sterilized with EtO (ethylene oxide). Sterilization by irradiation may also be performed, but the polymer may discolor. Many polymers may exhibit birefringence when molded. High birefringence can weaken the part, and can also reduce the optical performance of the part. It would therefore be desirable to provide a polymer such as COP or COC than can be molded with low birefringence.

Because of the desirable engineering properties of COC and COP, these polymers are promising for use in optical components such as in an illuminated surgical system like an illuminated retractor, laryngoscope, cannula, or the like. Use of COP will be discussed in many of the embodiments below, however, this is not intended to be limiting, and COC may also be used instead of COP.

Exemplary COC polymers include Mitsui Chemicals, Inc. APEL™ APL5514ML and APL5014DP optical grade molding resins. Table 1 below summarizes some of the material properties of APEL™. Because this material has the minimum birefringence and highest refractive index of COC polymers, and because it may be processed with injection molding, it is a good candidate for use in optical components such as lenses or light waveguides.

TABLE 1

| Property | APL5514ML | APL5014DP |
|---|---|---|
| Heat resistance (° C.) | | |
| $T_g$ (Mitsui method, DSC) | 135 | 135 |
| TMA (Mitsui method, softening point) | 147 | 147 |

TABLE 1-continued

| Property | APL5514ML | APL5014DP |
|---|---|---|
| Melt flowability (g/10 min) MFR (260° C., 2.16 kg) | 36 | 36 |
| Optical properties | | |
| Refractive index ($n_D$) | 1.54 | 1.54 |
| Abbe number | 56 | 56 |

Other exemplary COP polymers include Zeonex® and Zeonor® cyclo olefin polymers from Zeon Corporation (Tokyo, Japan). These COP polymers are desirable due to their optical properties, low water absorption, and high purity. Water absorption is less than 0.01%. Also, Zeonex® has a low specific gravity (approximately 1), thereby allowing optical components to be fabricated that are light weight. Also, Zeonex® COP has a relatively high heat resistance that is greater than acrylics such as polymethylmethacrylate (PMMA) while heat resistance is similar to that of polycarbonate (PC). COP also has excellent resistance to acidic and alkali chemicals, and is readily injection moldable. Several of the mechanical properties of various grades of Zeonex® and Zeonor® are summarized in Table 2 below. In addition to the mechanical and optical properties, some of the Zeonex® and Zeonor® COPs are also biocompatible based on testing conducted under ISO standard 10993 or under USP standards. A drug master file (DMF) has been established by the manufacturer.

TABLE 2

| Property | Zeonex® 480 | Zeonex® 480R | Zeonex® E48R | Zeonex® 330R | Zeonex® RS820 | Zeonor® 1020R | Zeonex® 690R | Zeonex® 790R |
|---|---|---|---|---|---|---|---|---|
| Specific gravity | 1.01 | 1.01 | 1.01 | 0.95 | 1.01 | 1.01 | 1.01 | 1.01 |
| Water absorption (%) | <0.01 | <0.01 | <0.01 | <0.01 | <0.01 | <0.01 | <0.01 | <0.01 |
| Light transmittance, (%), 3 mm thickness | 92 | 92 | 92 | 92 | White | 92 | 92 | 92 |
| Refractive index | 1.53 | 1.53 | 1.53 | 1.51 | — | 1.53 | 1.53 | 1.53 |
| Glass transition temperature, ° C. | 138 | 138 | 139 | 123 | 138 | 105 | 136 | 163 |
| Heat distortion temperature, ° C. (18.6 kgf/square cm, no annealing) | 123 | 123 | 122 | 103 | 123 | 101 | 136 | 161 |
| Tensile strength, MPa | 59 | 59 | 71 | 45 | 43 | 53 | 61 | 73 |

Table 3 below summarizes some of the mechanical and optical properties of various polycarbonate (PC) and polymethylmethacrylate (PMMA) polymers.

TABLE 3

| Property | PC Optical Grade | PC | PMMA |
|---|---|---|---|
| Specific gravity | 1.2 | 1.2 | 1.17-1.2 |
| Water absorption (%) | 0.2 | 0.15 | 0.3 |
| Light transmittance, (%), 3 mm thickness | 89 | 89 | 92-95 |
| Refractive index | 1.59 | 1.59 | 1.49 |
| Glass transition temperature, ° C. | 121 | 123-132 | 74-99 |
| Tensile strength, MPa | 63 | 67 | 49-77 |

Therefore, it would be desirable to provide a material such as COP or COC having a specific gravity greater than polycarbonate or PMMA (so the parts are lighter), and water absorption less than polycarbonate or PMMA. Water absorption affects index of refraction, therefore Zeonex and Zeonor are desirable since they are non-polar and hence hydrophobic with very low absorption. Additionally, it would be desirable to provide a material such as COP or COC that transmits light with greater efficiency than polycarbonate or greater efficiency or equal efficiency to that of PMMA. The COP or COC material also preferably has a glass transition temperature greater than polycarbonate or PMMA. At least some of the grades of COP or COC disclosed herein are also sterilizable with at least EtO without compromising optical properties of the component.

Retractor illumination system 10 of FIG. 1 includes blade retractor 12 including channel 13 to engage a fiber optic input 14 and waveguide illuminator 16. Latch 17 serves to mechanically attach waveguide illuminator 16 to fiber optic input 14 so that the resulting assembly may be moved up and down in channel 13 to any position suitable for illumination. The optical coupling between fiber input 14 and waveguide illuminator 16 is a simple face-to-face coupling, which may be enhanced by use of an index matching gel, or other similar material, applied to either the fiber input 14 or the waveguide illuminator 16 or both. Light entering waveguide illuminator 16 is contained within the waveguide with minimal light loss until it reaches output optical structures such as output structures 18, where light exits to illuminate the predetermined illumination area 20. Output optical structures 18 may include one or more stair stepped facets or lenses that may include a radius or angled face, one or more prism structures, one or more diffraction gratings, applied optical film, or other optical structures designed to direct the available light to the predetermined illumination area 20.

In the cross-section view of FIG. 1A channels 13 of blade 12 engage waveguide illuminator 16. Any suitable channel configuration may be used, such as, for example, a single channel with a circular or rhomboid cross-section. The section view of FIG. 1B shows a section of blade retractor 12, waveguide illuminator 16 and fiber input 14, with detail showing latch 17 which snaps into a hole or detent 14D formed in fiber input 14 and the latch may be disengaged with a minor amount of force. Output optical structures 18 control and direct output light energy 21 which illuminates predetermined illumination area 20.

Figure 2:
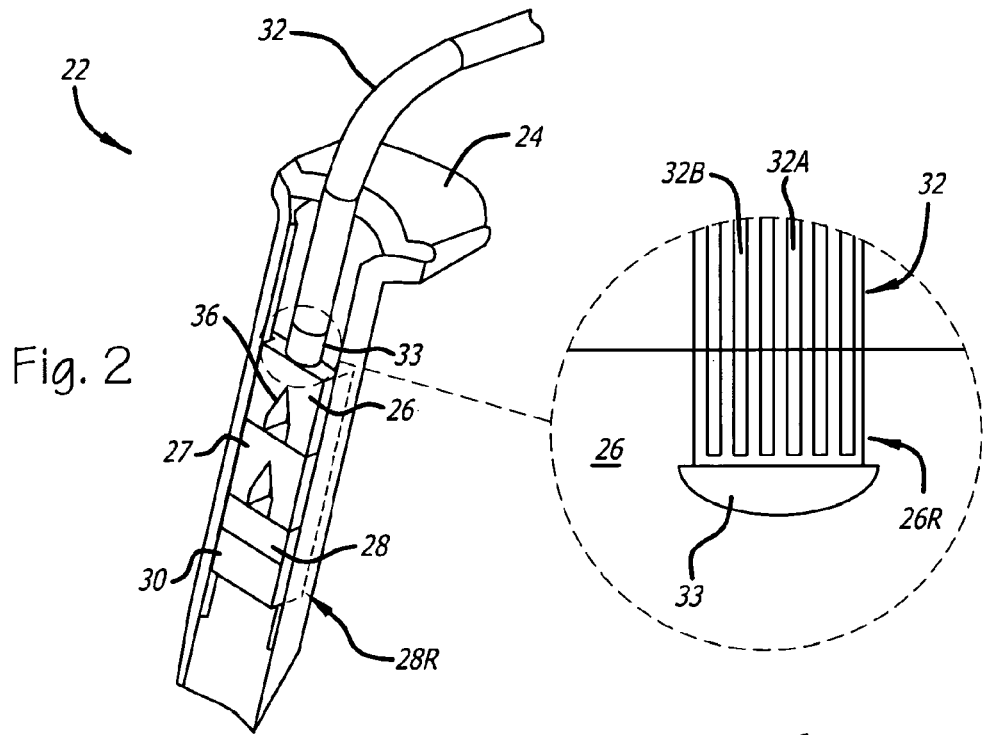
FIG. 2 is a perspective view of an alternate COP blade insert illuminator.

Alternate blade insert illumination system 22 of FIG. 2 includes blade retractor 24 that includes light input section 26, one or more light conduit sections such as light conduit section 27, and a light output section such a light output section 28 that includes one or more output optical elements such as output optical elements 30. In this configuration, light input section 26 has an integrated fiber optic input 32. One or more fiber optic strands such as strands 32A and 32B may be integrated into the upper portion of light input section 26 by molding the strands into light input section 26, gluing the strands into a formed receiving hole 26R formed into the section, or other suitable methods. A light coupling element such as element 33 may also be included to improve light coupling and distribution. A collar such as collar 34 may be provided to aid in strain relief for the optical fiber input. Light directing structure 36 causes the light coming into the center of the waveguide illuminator to be directed along the sides of light input section 26. The same light directing structure is shown in light conduit section 27, serving to direct the light down to the next section. Light input section 26 and light conduit section 27 may be provided without the light directing structure, but this may result in a decrease in efficiency.

Output optical element 30 may have a flat face to which an optical output film is applied to allow light to escape and direct the light toward tissues of interest, or output section 28 may have output optical film or molded structures located on or integrated into rear face 28R that serve to send light out through output optical element 30.

Figure 2A:
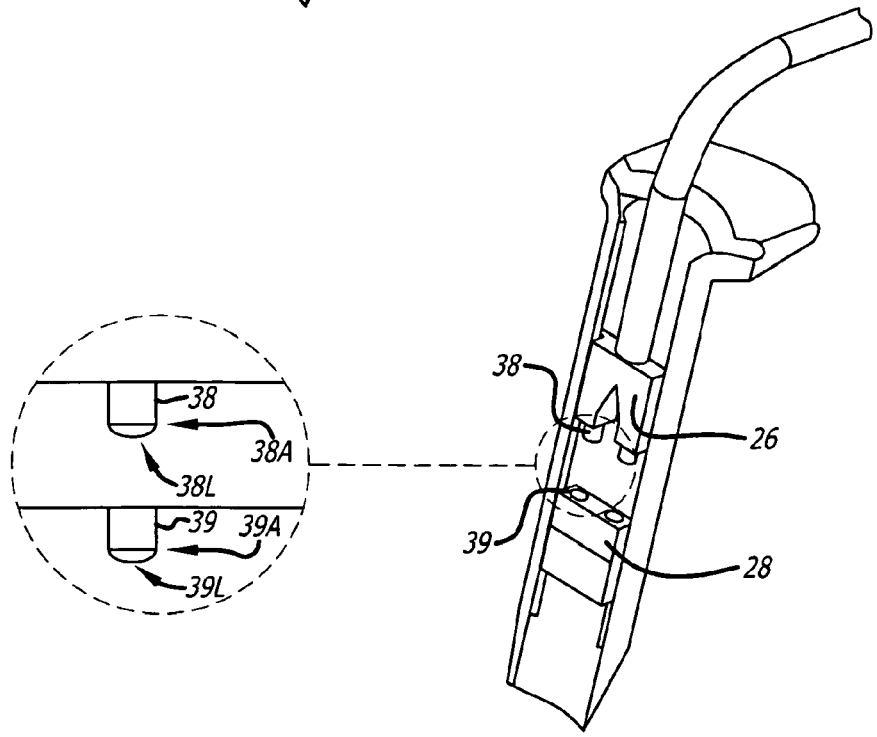
FIG. 2A is a perspective view of the attachment mechanism of the COP blade illuminator of FIG. 2.

FIG. 2A shows the blade insert illuminator system of FIG. 2 with light conduit section 27 removed to show the section attachment mechanism consisting of one or more male members such as engagement member 38 and a corresponding receptacle such as receptacle 39. Output end 38A of the male member 38 may also include one or more output transmission coupling structures or optical structures, e.g., a lens, such as lens 38L to focus the light into the corresponding receptacle. Bottom 39A of receptacle 39 may also include one or more input transmission coupling structures or optical structures, e.g., a lens, such as lens 39L to spread light into its corresponding waveguide. In use, the male members are pressed into the female receptacles of the subsequent section and friction holds the sections together.

In this configuration, light conduit section 27 of FIG. 2 may be removed, allowing light input section 26 and light output section 28 to be directly connected together, for example, to fit a blade having a short length or to permit adjustment along the blade retractor of the waveguide element to adjust the location of the illumination area. One or more light conduit sections 27 may be added to the assembly to fit blades of medium or long length thereby providing a modular blade insert illumination system whose components may be mixed and matched as needed. For example, if more than one blade retractor is used in a procedure, one blade may be fitted with a shorter assembly of blade illumination components to illuminate the upper part of the surgical field and a second blade may be fitted with a longer assembly of blade illumination system components to illuminate the lower, deeper part of the surgical field. Sliding a blade insert illumination system up and down slightly within the blade channel allows the illumination area to be adjusted, for example, sliding the light output section closer to the work area increases the intensity of illumination and sliding it away from the work area provides a more diffuse, less intense illumination. In this way, the modular blade insert illumination system may be optimized for a particular type of work to be performed.

FIG. 3 illustrates an alternate blade insert illumination system 40 inserted into blade 12. Blade insert illumination system 40 includes light input section 40A, one or more light conduit sections such as conduit sections 40B and light output section 40C. Bifurcated fiber optic cable 41 is integrated into light input section 40A. This blade illuminator configuration includes an engagement arm 42 and light directing structure 44.

FIGS. 3A, 3B and 3C illustrate details of arm 42 and light directing structure 44. When two or more modular elements of blade insert illuminator system 40 engage channels 13, the engagement arm 42 of first element 40B engages adjacent element 40A to maintain a secure optical connection at interface 45 between the elements. Arm 42 is a generally resilient member to permit flexing at joint 46 which permits tooth 47 to engage the light directing structure of the adjacent element. One or more light control elements such as light collecting lens 48 may be included at the input end of each blade illuminator element such as input end 49 of light output section 40C. Similarly, light output lens 50 may be included at the bottom, exit or output end 51 of a light conduit section such as conduit section 40B. Lenses 48 and 50 are illustrative of the use of optical structures to aid in the transmission of light between modules. Any other suitable optical structures such as angled facets, multi-faceted lens structures, spherical or aspherical lens may also be used. FIG. 3C illustrates how light travels in a blade insert illuminator conduit such as conduit element 40B. Light from bifurcated fiber optic cable 41 first enters the top of light input section 40A as illustrated in FIG. 3. Light energy 52 entering a blade illuminator waveguide such as conduit 40B, either from the fiber optic cable or light collecting lens 48, are guided by light directing structure 44 and light output lens 50.

Figure 4:
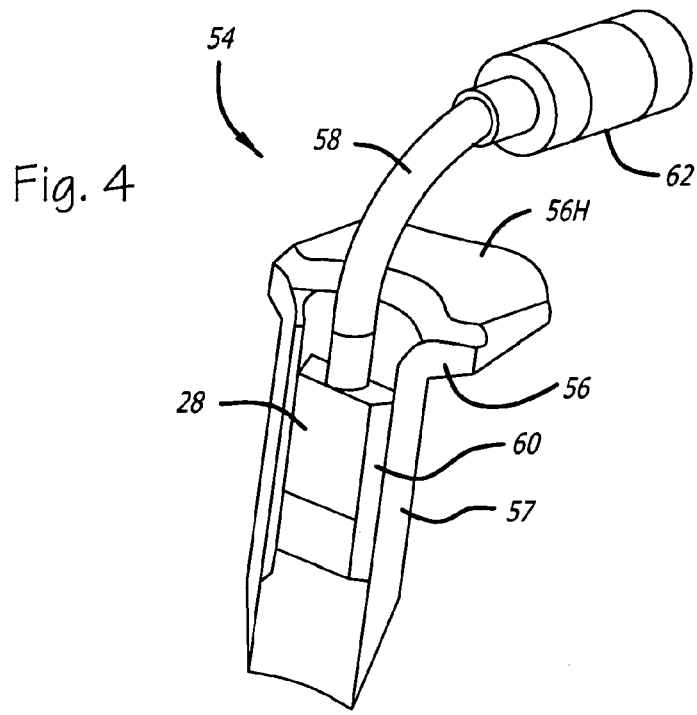
FIG. 4 is a perspective view of a single waveguide COP blade illuminator with a flexible input coupling for a short blade retractor.

Single element blade illuminator 54 is shown in FIG. 4. In this example, retractor 56 has a short blade 57. When used with a retractor having a long blade, single element blade illuminator 54 may be adjusted along the length of the retractor blade to provide illumination wherever it is needed.

In this configuration, a short section of fiber optic cable 58 is integrated into blade illuminator waveguide 60 at the output end and has any suitable connector 62 such as an industry standard ACMI connector or any other type of standard or proprietary connector, at the input end. Connector 62 is normally connected to a standard fiber optic light guide cable that conducts light from an external light source. Since blade insert illumination system 54 is made to minimize light loss, portable LED light sources may be attached directly to connector 62 or via a much shorter fiber optic light guide cable. Short section of fiber optic cable 58 is flexible and allows considerable latitude in how the connector 62 and light guide cable are oriented. For example, the connector 62 may be placed toward handle 56H of retractor 56 or it may be placed on either side in order to keep out of the way of the surgeon and any other equipment that may be in use.

Figure 5:
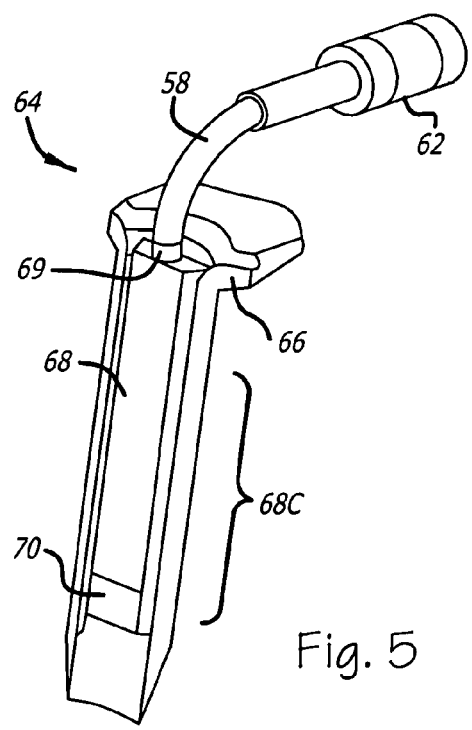
FIG. 5 is a perspective view of a single waveguide COP blade illuminator system with a flexible input coupling for a long blade retractor.

Single element extended blade illuminator system 64 of FIG. 5 is a simple blade insert illuminator designed to fit long blade retractors such a retractor 66. Illuminator waveguide 68 receives light at input 69, conducts light through total internal reflection throughout center portion 68C, and output optical structures such as output structure 70 directs the light toward a predetermined area to be illuminated.

Figure 5A:
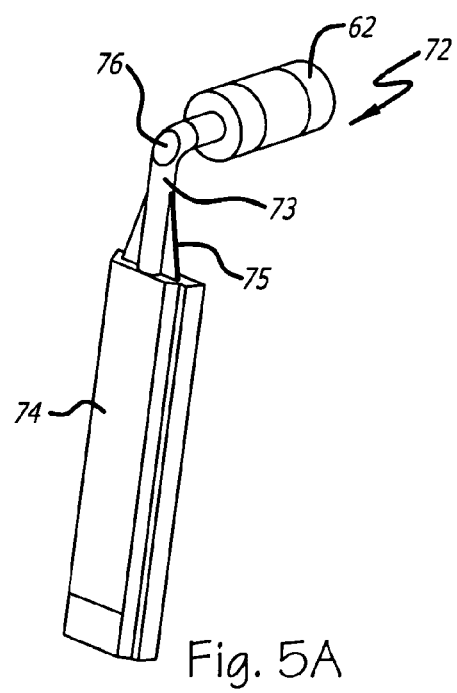
FIG. 5A is a perspective view of an alternate waveguide COP blade illuminator with a rigid input coupling.

FIGS. 4 and 5 illustrate that a blade insert illuminator may be provided in different sizes appropriate for the size of the retractor blade with which it is to be used. Blade insert illuminator 72 of FIG. 5A is an extended waveguide blade illuminator with a rigid light input component 73 in the place of the short section of fiber optic cable 58 as shown in FIGS. 4 and 5. Rigid light input component 73 allows all of the light guiding sections, waveguide 74 and rigid light input component 73, to be molded as one device, thereby reducing cost of the assembly. Support gussets or flanges such as flanges 75 may be added to provide stability. Flanges 75 may have a coating or film applied to prevent light from escaping or may be made from a different material, for example, using a co-molding or overmolding process. Rigid light input component 73 may have an orthogonal input as shown, requiring light directing structure 76 to direct light from connector 62 down to waveguide 74 of the waveguide illuminator. Rigid light input component 73 may also be formed with a radius, as shown in FIG. 5, and using total internal reflection to guide the light from connector 62 to the body of the waveguide. Rigid light input component 73 may also be made rotatable, thereby allowing the fiber optic light guide cable to be positioned as needed around the surgical field to avoid interference with other instruments.

Figure 6:
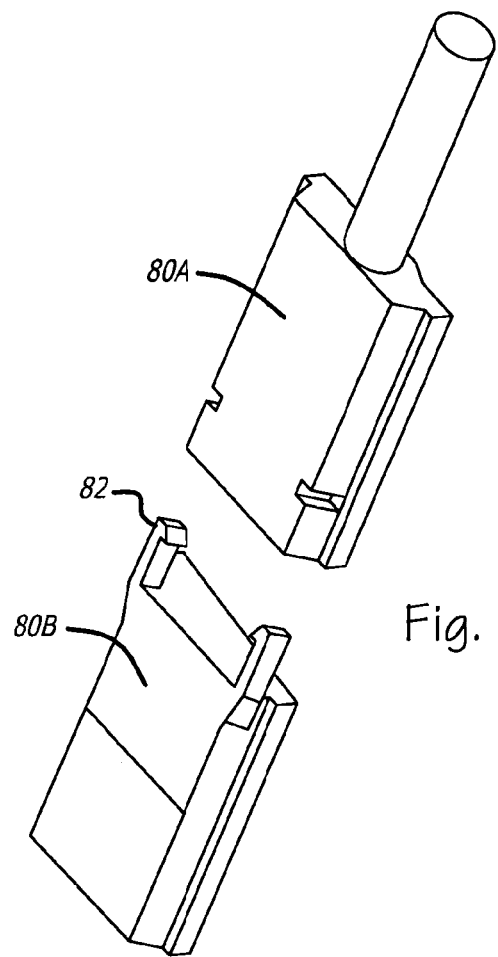
FIG. 6 is a perspective view of an alternate attachment mechanism for COP blade insert illuminator sections.

FIG. 6 illustrates alternate modular blade insert illuminator elements 80A and 80B showing an alternative placement of latches 82 that hold the waveguide components together. Keeping the latches off to the side of the components, rather than in front as shown in FIG. 3, reduces the likelihood of the latches being accidentally disengaged or broken by surgical instruments during the course of a surgical procedure. Any other suitable mechanisms may be used to attach the modular components to each other, e.g., dovetail joints, tongue-and-groove joints, adhesives that are preferably index matching adhesives, etc., to optimize light coupling from one module to the next. The attachment mechanisms may also be separate from the optical path, for example, metal pins and sockets may be located in optically inactive areas of the modules.

Figure 7:
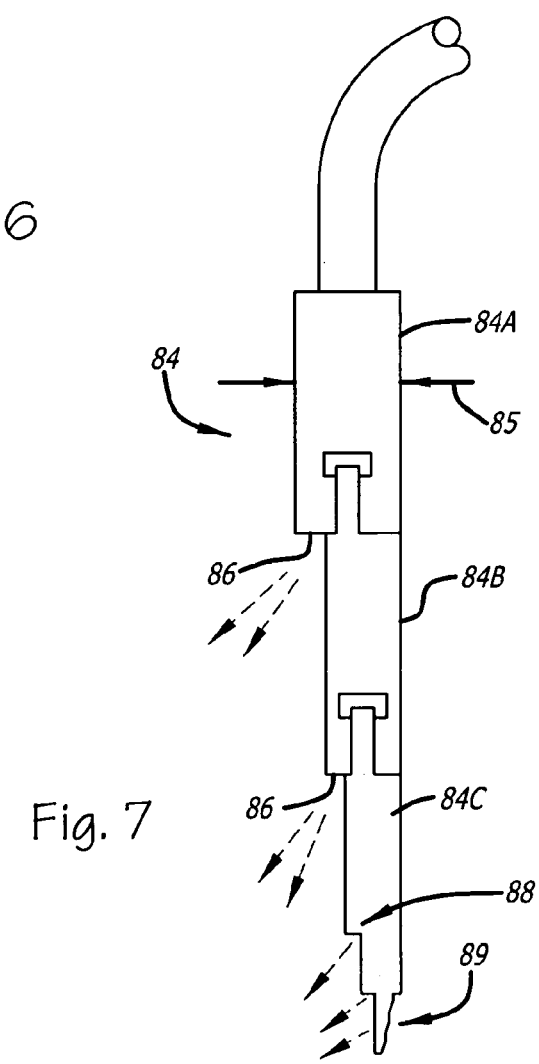
FIG. 7 is a side view of a COP blade insert illuminator with stepped waveguide sections.

FIG. 7 is a side view of an alternate modular blade insert illumination system 84 wherein each subsequent waveguide section is lessened in thickness 85. This allows output optical structures such as output structures 86 to be placed at the exposed end of the upstream waveguide, thereby allowing light to be directed from each waveguide section such as sections 84A, 84B, 84C. Each waveguide component such as sections 84A, 84B may have a bottom surface that contains output optical structures 86 over much of its surface to act as a terminal illumination component in case no other subsequent waveguide components are attached. Light output section 84C shows stepped output optical structure 88 on the front side and output optical structures 89 on the back side. Without output optical structures 88 that direct light out of the face, light would be lost out the end of light output section 84C, therefore, the combination of output optical structures 88 and 89 contribute to higher efficiency through less lost light.

Figure 8:
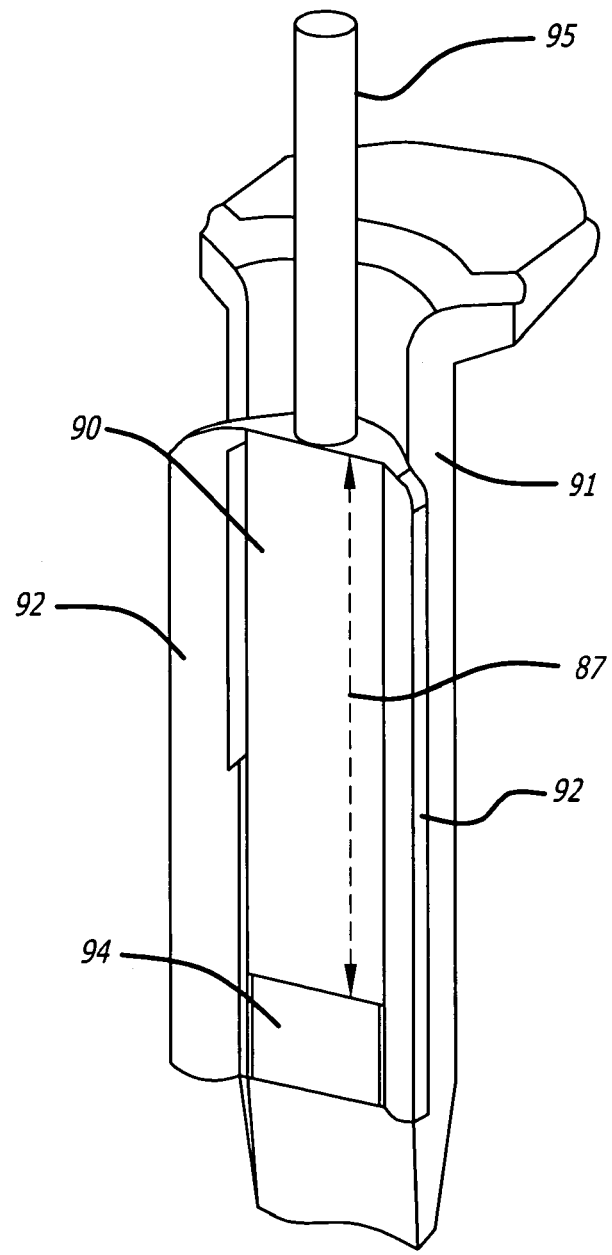
FIG. 8 is a perspective view of an alternate single waveguide COP blade insert illumination system.

Referring now to FIG. 8, winged blade insert illuminator 90 is shown engaged to retractor 91. Illuminator 90 has integrated wings 92 that may serve an additional retracting function. Wings 92 are oriented generally parallel to long axis 87 of illuminator 90. In this configuration, light is directed to exit output optical structure 94. Light enters illuminator 90 via light input component 95, which may be a fiber optic component or a rigid light conducting component at previously discussed. Because total internal reflection may allow light to enter wings 92, the wings may need a reflective coating to prevent light from exiting the wings and being lost or shining into unwanted directions, such as back into the surgeons eyes.

Figure 9:
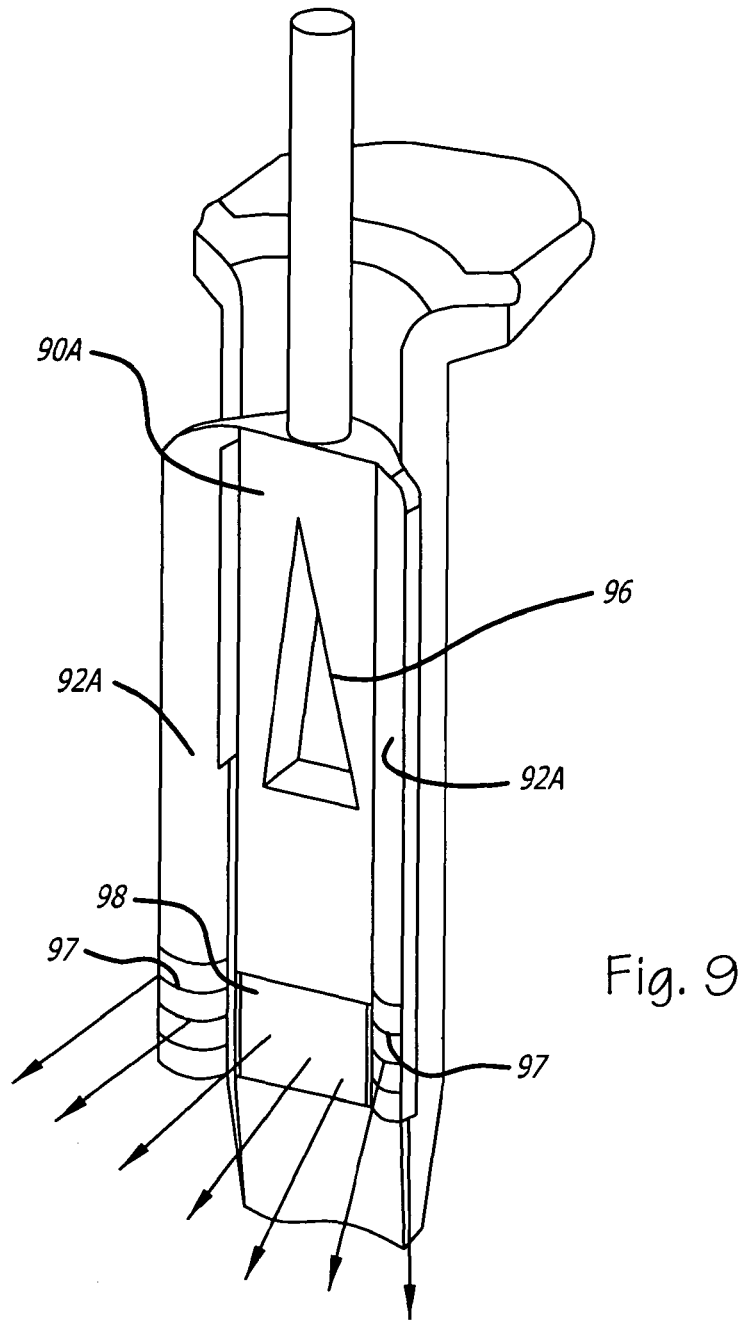
FIG. 9 is a perspective view of a single waveguide COP blade insert with a light directing structure.

FIG. 9 illustrates another alternate blade insert illuminator 90A that has a light directing element 96, which serves to direct the light coming into the middle of the illuminator out toward the wings 92A. Output optical structures such as structures 97 and 98 may be placed on wings 92A and body respectively to provide illumination from both structures as shown by the arrows.

Figure 10:
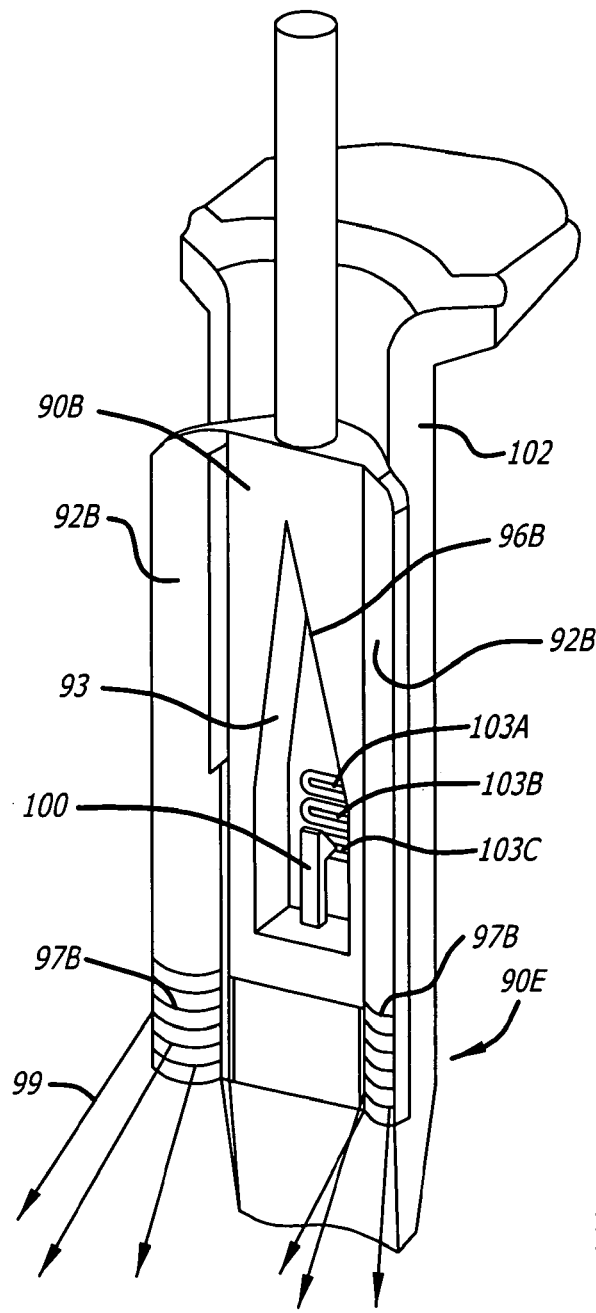
FIG. 10 is a perspective view of a single waveguide COP blade insert with a light directing structure with an attachment mechanism.

FIG. 10 illustrates another alternate blade insert illuminator 90B with an extended light directing element 96B. In this embodiment, optical output structures are placed only on the wings 92B so that illumination, light energy 99, only exits through extended output structures 97B in wings 92B as shown by the arrows. Extended light directing element 96B has reflective walls such as wall 93 that extend to output end 90E of illuminator 90B to maximize light reflected to the wings 92B. This configuration also includes alternative latch arm 100 oriented near the interface with retractor 102 to engage cutouts or detents such as detents 103A, 103B and 103C located in retractor 102. Latch arm 100 may be made of the same material as the waveguide or may be made of a different material for durability. For example, latch arm 100 may be made from steel or titanium and insert molded into illuminator 90B.

Alternatively, a retractor blade may be inserted into one or more slots in the illuminator waveguide to provide rigidity and or to enable cooperation with surgical site retention apparatus.

Figure 11:
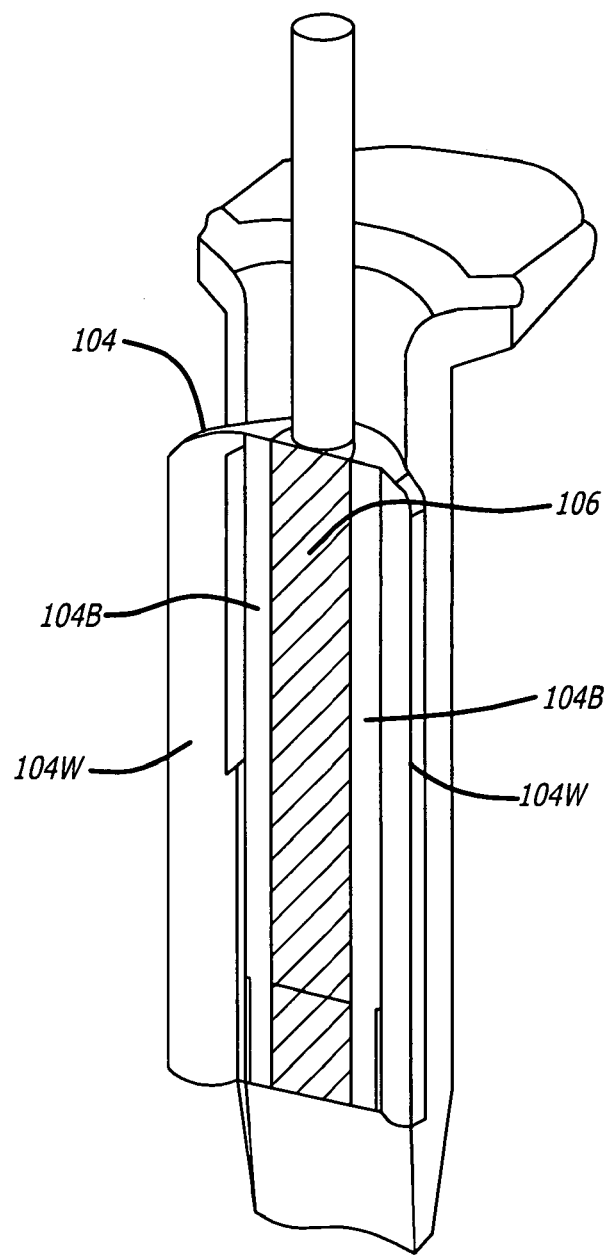
FIG. 11 is a perspective view of a single waveguide COP blade insert with a waveguide element co-molded with a retracting element.

Co-molded blade insert illuminator 104 of FIG. 11 includes waveguide section 106 has been co-molded or over-molded with wing and body retractor portions 104W and 104B respectively, which are made of a different material. For example, retractor wing and body portions 104W and 104B may be made of a stronger, glass reinforced plastic or steel or titanium for strength while waveguide section 106 is molded from cyclo olefin polymer.

Figure 12:
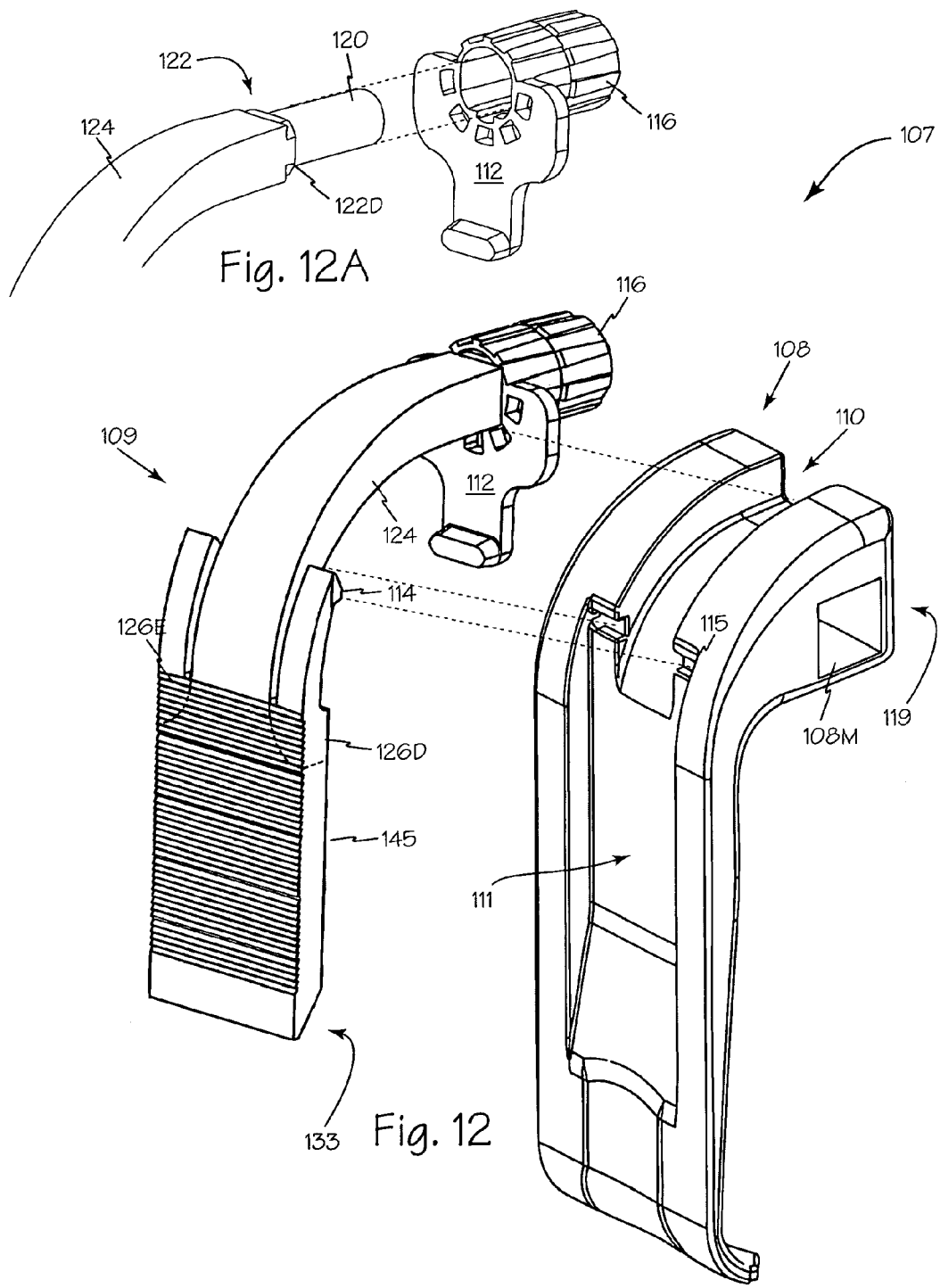
FIG. 12 is a perspective view of a COP illuminated retractor.

FIG. 12 illustrates a McCulloch style retractor adapted to provide light into the surgical field. Illuminated retractor 107 is composed of retractor blade 108 and illumination blade 109. Retractor blade 108 is shown as a McCulloch style retractor blade for use with a McCulloch retraction system although any suitable retractor and or retraction configuration may be used. Retractor blade 108 includes one or more mechanical connectors such a mechanical connector 108M and neck slot or channel 110 to accommodate neck zone 124 and blade slot 111 to accommodate output blade 125 within retractor blade 108 while maintaining an air gap between active zones of the illumination blade and the retractor. Two or more engagement elements such as blade or plate 112 and tabs 114 secure illumination blade 109 to retractor blade 108. Each tab 114 engages one or more engagement receptacles such as receptacles or recesses 115. Plate 112 is joined to collar 116, and when collar 116 removably engages input dead zone 122D, the collar surrounds illumination blade input 118. The removable engagement of collar 116 to input dead zone 122D also brings plate 112 into contact with end surface 119 of the retractor blade. Collar 116 securely engages dead zone 122D and surrounds cylindrical input zone 120 and forms input air gap 120G. Engagement at dead zones minimizes interference with the light path by engagement elements such a plate 112 and tabs 114. Plate 112 engages end surface 119 and tabs 114 resiliently engage recesses 115 to hold illumination blade 109 fixed to retractor blade 108 without contact between active zones of illumination blade 109 and any part of retractor blade 108.

Illumination blade 109 is configured to form a series of active zones to control and conduct light from illumination blade input 118 of the cylindrical input zone 120 to one or more output zones such as output zones 127 through and output end 133 as illustrated in FIGS. 12, 13, 14 and 15. Illumination blade 109 also includes one or more dead zones such as zones 122D, 126D and 126E. Dead zones are oriented to minimize light entering the dead zone and thus potentially exiting in an unintended direction. As there is minimal light in or transiting dead zones they are ideal locations for engagement elements to secure the illumination blade to the retractor.

Light is delivered to illumination blade input 118 using any conventional mechanism such as a standard ACMI connector having a 0.5 mm gap between the end of the fiber bundle and illumination blade input 118, which is 4.2 mm diameter to gather the light from a 3.5 mm fiber bundle with 0.5 NA. Light incident to illumination blade input 118 enters the illumination blade through generally cylindrical, active input zone 120 and travels through active input transition 122 to a generally rectangular active retractor neck 124 and through output transition 126 to output blade 125 which contains active output zones 127 through 131 and active output end 133. Retractor neck 124 is generally rectangular and is generally square near input transition 122 and the neck configuration varies to a rectangular cross section near output transition 126. Output blade 125 has a generally high aspect ratio rectangular cross-section resulting in a generally wide and thin blade. Each zone is arranged to have an output surface area larger than the input surface area, thereby reducing the temperature per unit output area.

Figure 13:
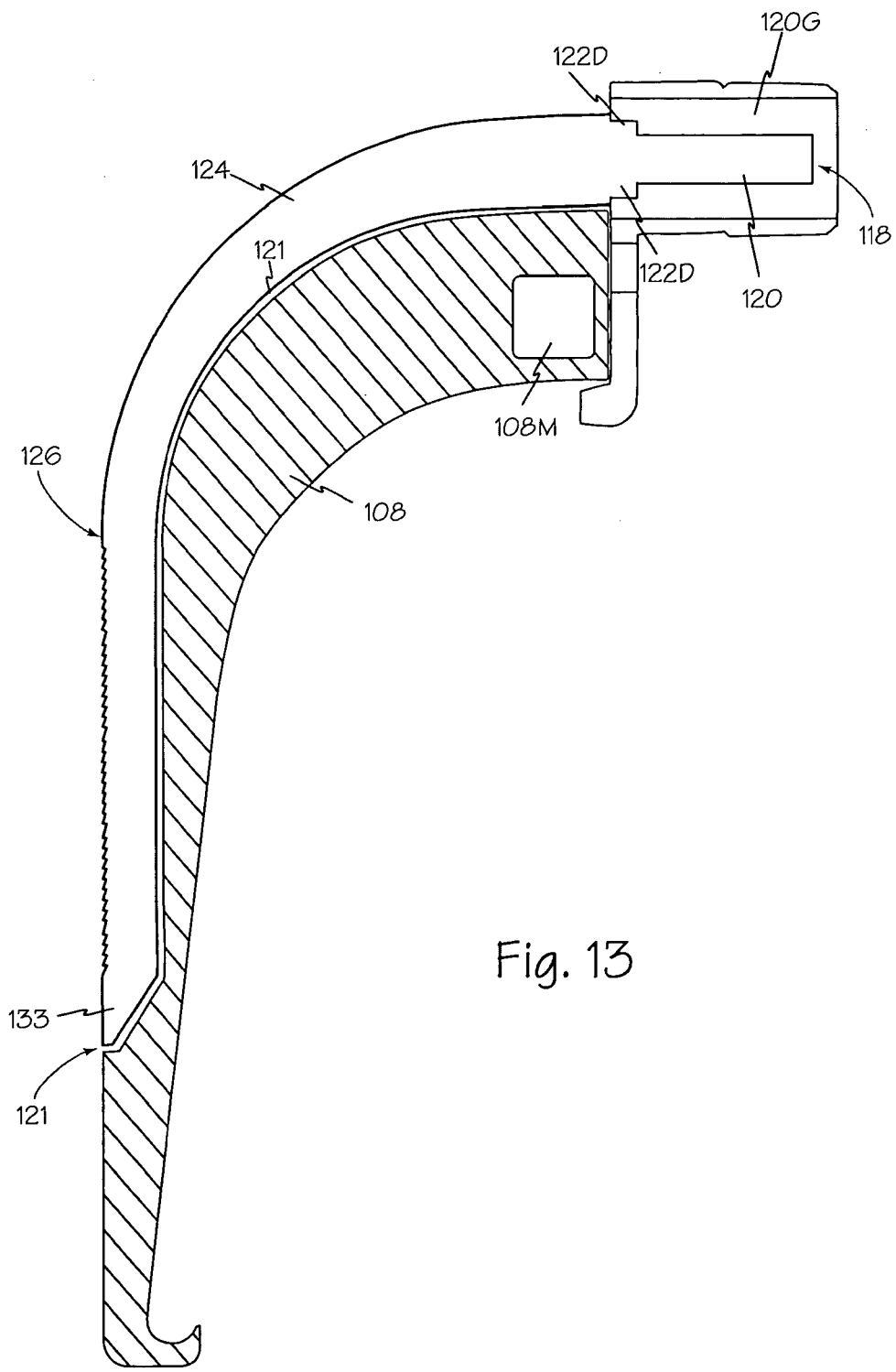
FIG. 13 is a cross-section view of the COP illuminated retractor of FIG. 12.

In the illustrated configuration illumination blade 109 includes at least one dead zone, dead zone 122D, generally surrounding input transition 122. One or more dead zones at or near the output of the illumination blade provide locations to for engagement elements such as tabs to permit stable engagement of the illumination blade to the retractor. This stable engagement supports the maintenance of an air gap such as air gap 121 adjacent to all active zones of the illumination blade as illustrated in FIG. 13. Neck zone 124 ends with dimension 132 adjacent to output transition 126 which extends to dimension 134 at the output zones. The changing dimensions result in dead zones 126D and 126E adjacent to output transition 126. These dead zones are suitable locations for mounting tabs 114 to minimize any effects of the engagement elements on the light path.

To minimize stresses on the light input and or stresses exerted by the light input on the illumination blade, the engagement elements are aligned to form an engagement axis such as engagement axis 136 which is parallel to light input axis 138.

Output zones 127, 128, 129, 130 and 131 have similar configurations with different dimensions. Referring to the detailed view of FIG. 14, the characteristics of output zone 127 are illustrated. Each output zone is formed of parallel prism shapes with a primary surface or facet such a primary facet 140 with a length 140L and a secondary surface or facet such as secondary facet 142 having a length 142L. The facets are oriented relative to plane 143 which is parallel to and maintained at a thickness or depth 144 from rear surface 145. In the illustrated configuration, all output zones have the same depth 144 from the rear surface.

The primary facets of each output zone are formed at a primary angle 146 from plane 143. Secondary facets such as facet 142 form a secondary angle 147 relative to primary facets such as primary facet 140. In the illustrated configuration, output zone 127 has primary facet 140 with a length 140L of 0.45 mm at primary angle of 27° and secondary facet 142 with a length 142L of 0.23 mm at secondary angle 88°. Output zone 128 has primary facet 140 with a length 140L of 0.55 mm at primary angle of 26° and secondary facet 142 with a length 142L of 0.24 mm at secondary angle 66°. Output zone 129 has primary facet 140 with a length 140L of 0.53 mm at primary angle of 20° and secondary facet 142 with a length 142L of 0.18 mm at secondary angle 72°. Output zone 130 has primary facet 140 with a length 140L of 0.55 mm at primary angle of 26° and secondary facet 142 with a length 142L of 0.24 mm at secondary angle 66°. Output zone 131 has primary facet 140 with a length 140L of 0.54 mm at primary angle of 27° and secondary facet 142 with a length 142L of 0.24 mm at secondary angle 68°.

Output end 133 is the final active zone in the illumination blade and is illustrated in detail in FIG. 14. Rear reflector 148 forms angle 149 relative to front surface 150. Front surface 150 is parallel to rear surface 145. Terminal facet 151 forms angle 152 relative to front surface 150. In the illustrated configuration, angle 149 is 32° and angle 152 is 95°.

Other suitable configurations of output structures may be adopted in one or more output zones. For example, output zones 127 and 128 might adopt a concave curve down and output zone 129 might remain generally horizontal and output zones 130 and 131 might adopt a concave curve up. Alternatively, the plane at the inside of the output structures, plane 143 might be a spherical section with a large radius of curvature. Plane 143 may also adopt sinusoidal or other complex geometries. The geometries may be applied in both the horizontal and the vertical direction to form compound surfaces.

In other configurations, output zones may provide illumination at two or more levels throughout a surgical site. For example, output zones 127 and 128 might cooperate to illuminate a first surgical area and output zones 129 and 130 may cooperatively illuminate a second surgical area and output zone 131 and output end 133 may illuminate a third surgical area. This configuration eliminates the need to reorient the illumination elements during a surgical procedure.

Figure 16:
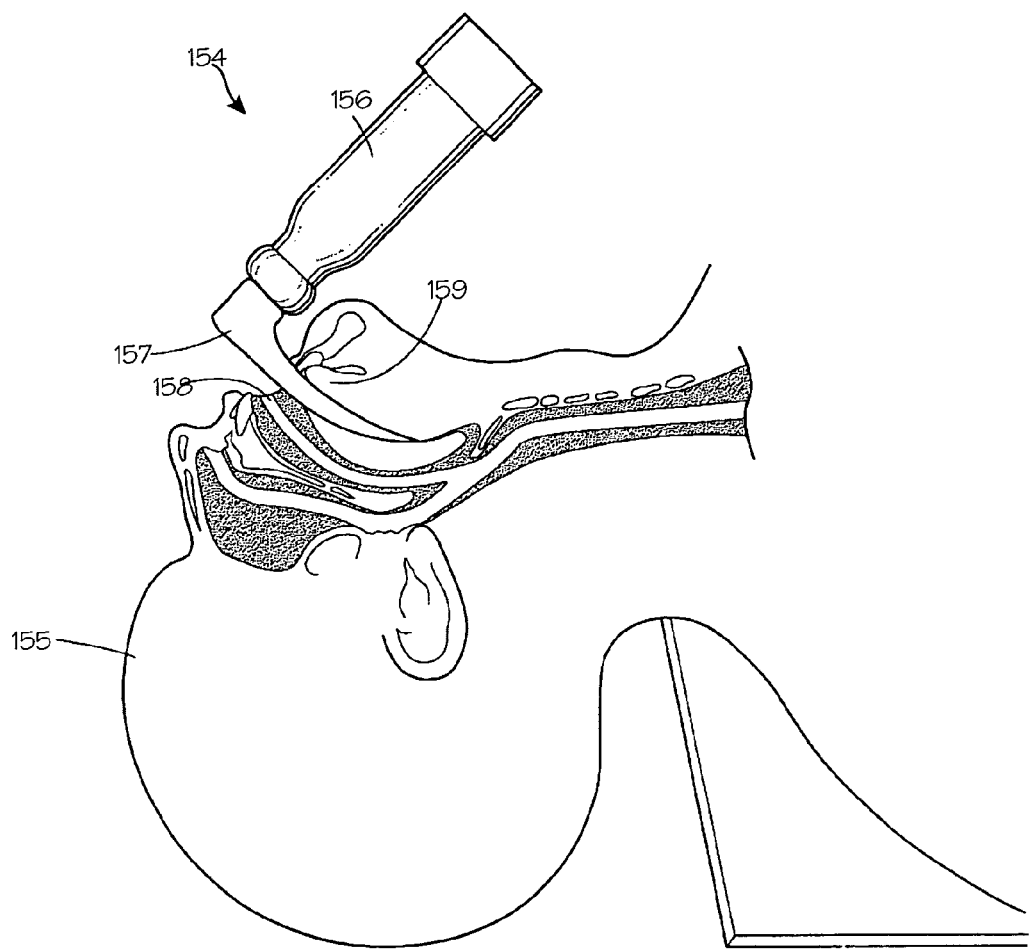
FIG. 16 is a side view of a COP laryngoscope cavity illuminator in use.

FIG. 16 illustrates COP laryngoscope illuminator 154 in use on a patient 155. Laryngoscope 154 includes a handle 156 and a blade 157. The handle 156 allows for grasping the laryngoscope 154. The blade 157 is rigid and is attached to and extending from the handle. The blade is formed of cyclo olefin polymer that acts as a waveguide and further includes an illumination source. Blade 157 is for inserting into mouth 158 of a patient to allow viewing of a portion of the mouth, the pharynx, and the larynx of the patient 155. Blade 157 is used to depress tongue 159 and mandible in order to prevent the tongue 159 of the patient 155 from obstructing the view of the medical professional during examination. When the illumination source is illuminated, electromagnetic waves (light) are able to propagate through blade 157 and illuminate the mouth and trachea of the patient.

FIG. 17 illustrates the laryngoscope 154 of the laryngoscope illumination system in further detail. The laryngoscope 154 includes a handle 156 and a blade 157. Blade 157 is formed of cyclo olefin polymer that acts as a waveguide. Blade 157 may have an illumination source disposed therein. The illumination source disposed within the blade comprises one or more LEDs 161 (light emitting diodes), battery 162, a conductor 163 electrically connecting the battery and the LED, and an LED control circuit 164 and switch 165. The LED is preferably a white-light LED, which provides a bright, white light. The battery may be provided in any form, but is preferably a lithium ion polymer battery. Blade 157 may also be detachable from the handle and disposable. The illumination source is in optical communication with the blade. When the illumination source is illuminated, light from the illumination source propagates through the blade illuminating predefined areas adjacent to the blade.

FIG. 18 illustrates an alternate laryngoscope illumination system with the illumination source in the handle of the laryngoscope 154. The laryngoscope 154 includes a handle 156 and a blade 157. Blade 157 is formed of cyclo olefin polymer and performs as a waveguide. Handle 156 has an illumination source disposed therein. The illumination source disposed within the handle comprises one or more LEDs 161 (light emitting diodes), battery 162, a conductor 163 electrically connecting the battery 162 and the LED 161, an LED control circuit 164, a switch 165 and an optical fiber 166 in optical communication between the LED 161 and the blade 157 for conducting light output 167 from the LED 161 to the blade 157.

The light output 167 of the optical fiber travels to one or more light directing surfaces such as surface 168 where it is directed toward output optical structures 169 on any suitable surface of the blade. Output optical structures 169 may direct illumination to particular anatomical areas through refraction while minimizing reflection that contributes to loss of light. The LED is preferably a white-light LED, which provides a bright, white light. The battery may be provided in any form, but is preferably a lithium ion polymer battery. The optical fiber 166 is secured in a channel provided in the laryngoscope 154. LED 161 may be positioned in closer proximity to blade 157 such that light from LED 161 is captured directly by blade 157, perhaps using optical structures on the light input portion of blade 157 that efficiently capture light from LED 161, thereby obviating the need for optical fiber 166. The handle 156 of this laryngoscope may serve as a heat sink for dissipating the heat generated by the LED, and additional heat sinks structures may be added. The handle may also be manufactured and provided separately from the blade of the laryngoscope 154. This way, the blade 157 may be packaged separately from the handle to enable disposable use of the blade 157 with a non-disposable handle 156. When the illumination source is illuminated, light from the illumination source propagates through the optical fiber to the blade illuminating the blade 157. This in turn can illuminate the mouth and trachea of a patient.

Cavity illuminator 172 of FIG. 19 includes a COP waveguide insert 174 attached to blade 175. The waveguide insert may be attached to the blade surface, e.g., with a suitable adhesive or other attachment means, or may be inserted into a channel formed in the blade to receive and hold the insert. The blade and handle may be separate pieces or integrated as a single device. In this embodiment, light from optical fiber 166 injects light into waveguide insert 174, said light traveling along the waveguide insert to exit at one or more optical output structures positioned at one or more designated areas of the waveguide insert. Optical fiber 166 may be replaced by any other suitable light conduit, such as a rigid or flexible light pipe or waveguide.

Referring now to FIGS. 20 and 21, cavity illumination system 178 includes COP waveguide insert 179, the waveguide insert having an input connector 180 to couple light into the waveguide insert from an external light source, such as a fiber optic cable connected to any suitable light source such as a xenon or tungsten light source. Waveguide insert 179 may engage a channel 175c in the blade. The channel is designed to engage the insert. The waveguide insert is formed of cyclo olefin polymer. The waveguide may be made to be single use disposable or made to be suitable for multiple uses. The light source contained in the blade injects light into the waveguide insert, said light then is contained in the waveguide and travels to output optical structures in the waveguide insert that direct light to particular anatomic areas.

Waveguide insert 179 as shown in FIG. 22 may include output optical structures such as structures 182 in one or more suitable locations to direct light 184 to any appropriate anatomical areas. Output optical structures 182, here, stair stepped facets such as facet 182F, running a portion of the length of the top surface 186T of the waveguide insert, each of facets 182F causing a portion of the light 184 to exit the waveguide insert in a predetermined direction while minimizing light lost due to reflection at these structures in order to maintain high transmission efficiency. If the output optical structures abruptly end at an end face, light will shine out of this end face. However, the light that exits the end face may not serve as useful illumination and, hence, may be considered lost light that lessens the efficiency of the waveguide insert. To improve efficiency, one or more optical structures 187 may be arranged on bottom surface 186B of to direct light out of the corresponding top surface 186T, which may have microstructured optical components to diffuse or further direct the output light 188. Combining the bottom face output optical output structures 187 with the top face output optical structures 182 increases the transmission efficiency of the waveguide insert.

FIG. 23 is a side view of a COP speculum illumination system in a closed or insert position. Gynecological speculum 190 includes a first handle 191, a second handle 192, an upper blade 193 and lower blade 194. The upper blade 193 and lower blade 194 are formed of cyclo olefin polymer that functions as a waveguide. Each blade may engage an illumination source or have an illumination source disposed therein. The illumination source disposed within the blades comprises one or more LEDs 196 (light emitting diodes), battery 197, a conductor 198 electrically connecting the battery and the LED, and an LED control circuit 199 and switch 200. The LEDs such as LED 196 are preferably a white-light LED, which provides a bright, white light. Battery 197 may be provided in any form, but is preferably a lithium ion polymer battery. The blades may also be detachable from the handle and disposable. The illumination source is in optical communication with the respective blade. When the illumination source is illuminated, light from the illumination source propagates through the blade providing illumination from appropriate areas of the blade.

Referring now to FIG. 24, handles 191 and 192 are closed to separate blades 193 and 194. In this orientation, blades 193 and 194 may direct light into any cavity in which the device is engaged. Any suitable structure, or structures such as coating 201, facets 202 and or micro optical structures 203 may be incorporated into blades 193 and or 194 to control and direct illumination, however, such structure or structures must be specifically designed to maximize light transmission efficiency and minimize light loss and must be specifically designed to direct light to specific anatomic structures. For example, structures 202 may designed to direct more diffuse light to illuminate a substantial portion of the vaginal wall, or may be designed to direct more focused light to illuminate the cervix at the end of the vaginal cavity, or may be designed to provide both types of illumination. Single or multiple refractive and/or reflective structures, which may be combined with microstructured optical components, may be used to maximize light transmission efficiency to allow lower power light sources to be used, thereby reducing heat generation and the need to provide cumbersome heat management devices and methods.

FIG. 25 illustrates an alternate COP cavity illumination system with the illumination source in first handle 204 and second handle 206 of the speculum 210. The speculum 210 includes a first handle 204 engaging upper blade 205, and a second handle 206 engaging lower blade 207. The upper and lower blades 205 and 207 are formed of cyclo olefin polymer that functions as a waveguide. Handles 204 and 206 have an illumination source disposed therein. The illumination source disposed within one or both handles comprises one or more LEDs such as LED 211 (light emitting diodes), battery 212, a conductor 213 electrically connecting the battery and the LED, an LED control circuit 214, a switch 215 and an optical fiber 216 in optical communication between the LED and a blade such as upper blade 205. The optical output of the optical fiber 216 travels through the blade illuminating the anatomical area(s) of interest. The LED is preferably a white-light LED, which provides a bright, white light. The battery may be provided in any form, but is preferably a lithium ion polymer battery. The optical fiber is secured in a channel provided in the speculum. The handles of this speculum may serve as a heat sink for dissipating the heat generated by the LED, and additional heat sinks structures may be added. The handles may also be manufactured and provided separately from the blades of the speculum. This way, the blades may be packaged separately from the handle to enable disposable use of the blade with a non-disposable handle. When the illumination source is illuminated, light from the illumination source propagates through the optical fiber to the blades illuminating the upper blade and lower blade. This in turn can illuminate the vaginal cavity or any other cavity of a patient.

Speculums with metal blades continue to be used. If a metal speculum is preferred, then a disposable waveguide insert, similar to that shown in FIG. 19 or FIG. 20, may be provided.

Speculum 220 of FIG. 26 may be a disposable speculum comprised of a COP illuminating bottom blade 221 (waveguide blade) and a non-illuminating top blade 222. Waveguide blade 221 has an input connector 224 for a suitable light source, such as a fiber optic cable 225 connected to an external xenon light source 226. Light 228 enters the connector portion of the waveguide blade and travels up the handle portion to a light directing structure 230, which directs the light 90 degrees toward the output optical structures 231 and 232 located along the bottom blade portion.

If COP blade 221 has a solid cross-section as shown in FIG. 26A, output optical structures such as structures 231 and 232 may extend the full width 234 of blade 221 as well. If the COP blade has a concave or cup-shaped cross-section as shown in FIG. 26B, separate output optical structures may be located on edge faces 235 and 236 as well as on concave surface 237. The output optical structures direct light to specific anatomic areas and such light may be more diffuse, more focused, or a combination of each.

Cavity illumination system 238 of FIG. 27 may include two COP waveguide blades, 221 and 239. The bottom waveguide blade 221 is as described for FIG. 26. Top waveguide blade 239 may include a connector 240 for a separate light source or both the top and bottom waveguide blades may be connected to the same light source 241. Top waveguide blade 239 may not need internal light directing structures, such as structure 230 in blade 221, because its normal geometry may provide suitable reflecting surfaces for directing light 242 toward the output optical structures 239*a* and 239*b*. Top waveguide blade may have a similar output optical structure as the bottom waveguide blade. Together, the two blades provide even illumination of the entire cavity wall. Alternatively, each blade may have different output optical characteristics to provide complimentary illumination, each blade illuminating different areas or anatomy or providing illumination energy of different wavelengths.

FIG. 28 illustrates a side view of a COP illuminating anoscope waveguide 250 with a proximal end 251 and a distal end 252 that is inserted into a patient's natural cavity such as the anal cavity. The anoscope waveguide 253 may also be used as a general speculum. The anoscope waveguide is formed of cyclo olefin polymer. It may also include an input connector 254 that serves to conduct light into the waveguide such that light is conducted around the entire circumference 255 of the waveguide tube. Output optical structures 256 are typically placed near the distal end on the inside wall 257 along all or a portion of circumference 255. Output optical structures placed on the end face 258 or outside wall 259 might cause irritation to the cavity walls during insertion. If output optical structures are required on end face 258 or outside wall 259, any suitable coating or material may be used to lessen the irritation to the patients body tissue during insertion of the waveguide. The output optical structures provide even illumination of the entire cavity wall. A reflective or prismatic surface may also be created on the proximal end face to send mis-reflected light rays back toward the distal output optical structures.

Referring now to FIG. 29 shows an example of a light directing structure that contributes to light distribution around circumference 255. Light entering input connector 254 may be directed by a light control structure, such as structure 260, which splits the incoming light and sends it down into the waveguide tube wall at an angle ensuring circumferential light distribution.

Figure 30:
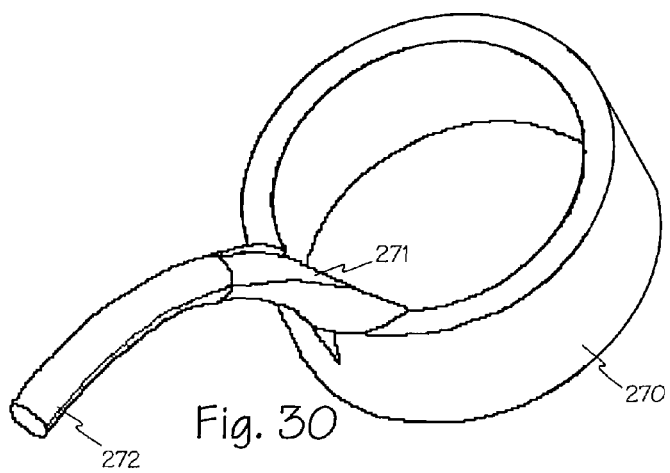
FIG. 30 is a perspective view of a COP optical waveguide with a curved input light coupling.

Referring now to FIG. 30, optical waveguide 270 may include an alternate light coupling apparatus such as coupling 271. Coupling 271 may provide mechanical support and optical conduit between optical input 272 and waveguide 270.

Figure 31:
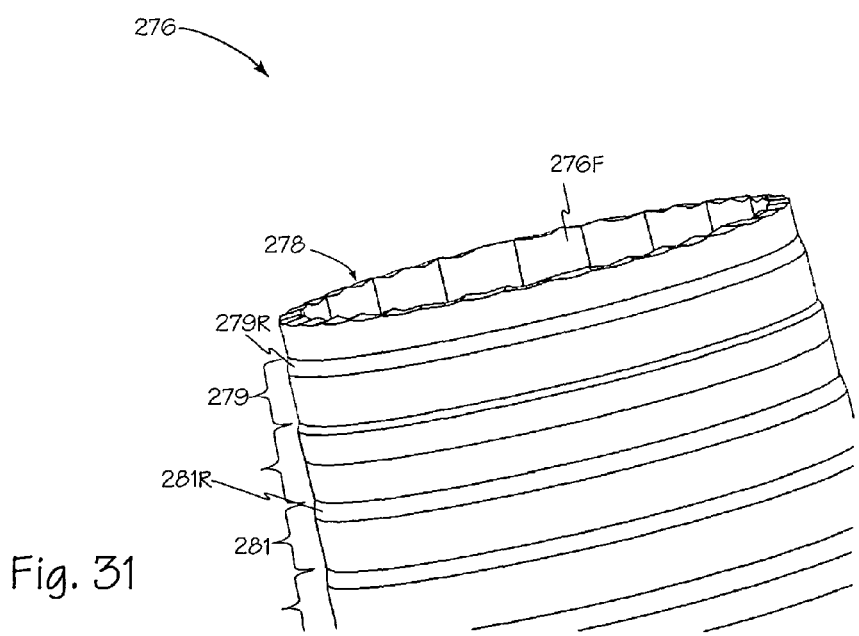
FIG. 31 is an enlarged perspective view of the distal end of the COP optical waveguide of FIG. 30.

Distal end 276 as shown in FIG. 31 includes one of more vertical facets such as facet 276F within the distal end to disrupt the light spiraling within the waveguide. Also shown are structures such as structure 278 on the end face of the cannula which serve to direct light as it exits the end face. Shown are convex lenses, but concave lenses or other optical structures (e.g., stamped foil diffuser) may be employed depending on the desired light control. Stepped facets such as facets 279 and 281 are shown on the outside tube wall. The "riser" section, risers 279R and 281R respectively, of the stepped facet is angled to cause the light to exit and as a result the waveguide slides against tissue without damaging the tissue. The angle is generally obtuse relative to the adjacent distal surface. Steps may be uniform or non-uniform as shown (second step from end is smaller than the first or third step) depending on the light directional control desired. The steps may be designed to direct light substantially inwards and or toward the bottom of the tube or some distance from the bottom of the tube, or they may be designed to direct light toward the outside of the tube, or any suitable combination. The facets such as facets 87 and 89 may be each designed to direct light at different angles away from the waveguide and or may be designed to provide different beam spreads from each facet, e.g., by using different micro-structure diffusers on each facet face.

Facets may be used on the inside surface of the COP waveguide, but if waveguide material is removed to form the facets, the shape of the waveguide may be changed to maintain the internal diameter of the bore generally constant to prevent formation of a gap is between the waveguide and a dilator tube used to insert the waveguide into the body. Said gap may trap tissue, thereby damaging it during insertion into the body or causing the waveguide to be difficult to insert. Thus the outer wall of the waveguide may appear to narrow to close this gap and prevent the problems noted.

Figure 32:
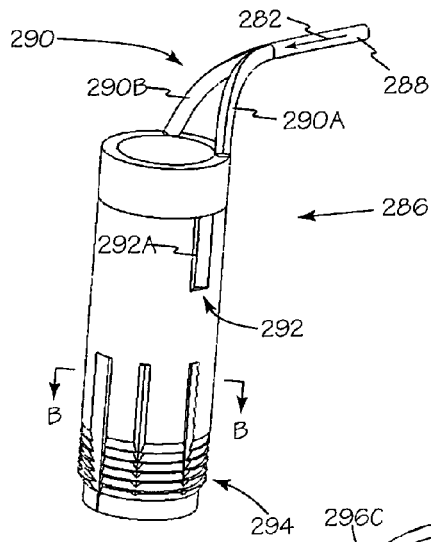
FIG. 32 is a perspective view of a COP optical waveguide with a split input coupling.
Figure 33:
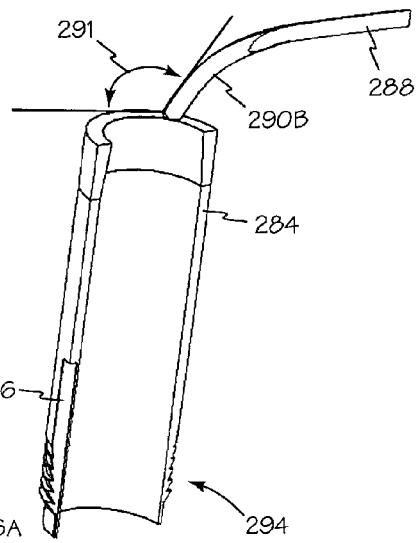
FIG. 33 is cutaway view of the COP optical waveguide of FIG. 32.
Figure 34:
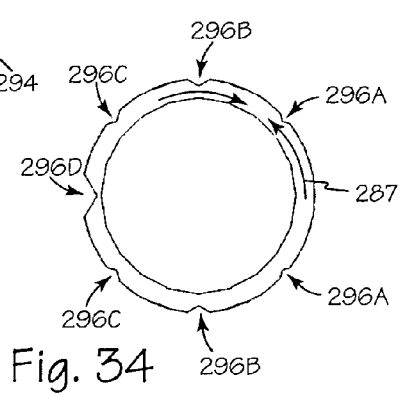
FIG. 34 is a cross-section of the COP optical waveguide of FIG. 32 taken along B-B.

Referring now to FIGS. 32, 33 and 34, applied light energy 282 may be bifurcated to send light into wall 284 of COP waveguide or tube 286. Light input 288 may be split in input coupling 290.

The bifurcated ends 290A and 290B of input 288 preferably enter tube wall 284 at an angle 291 to start directing light around the tube wall. Alternatively, the bifurcated ends 290A and 290B may each enter tube wall 284 at different angles to further control light distribution. The bifurcated ends may enter the tube wall orthogonally, but this may require a prism structure in the wall placed between the input and the output with the apex of the prism pointed at the input. The prism structure directs the light around the tube wall. A vertical prism structure, prism 292 is shown with apex 292A of the prism pointed in toward the center of the tube. Prism structure 292 may direct a portion of the input light back underneath the inputs and contributes to directing light all the way around the tube wall. The position, angle and size of this prism relative to the input bifurcated end determines how much light continues in the tube wall in its primary direction and how much light is reflected in the opposite direction in the tube wall.

Additional vertical prism structures or light disruption structures may be placed toward the bottom of the tube on the outside tube wall as shown in FIGS. 32, 33 and 34. One or more light extraction structures 294, shown as circumferential grooves cut into the outside wall of the tube, may also be included to optimize the illumination provided below waveguide 286. Light 287 traveling circumferentially in the tube wall will not strike the light extraction structures 294 with sufficient angle to exit waveguide 286. Thus, vertical prism 296 or light disruption structures such as disruption prisms 296A, 296B, 296C and 296D may be necessary to redirect the light so that the light rays 287 will strike light extraction structures 294 and exit the tube wall to provide illumination. As shown in FIG. 34, vertical prism structures such as 296A and 296B have different depths around the circumference in order to affect substantially all of the light rays traveling circumferentially in the tube wall. Vertical prisms of constant depth would not affect substantially all of the light rays.

FIG. 33 also illustrates how a COP half-tube may be formed to provide illumination. At least one COP half-tube illuminator may be attached to the end of at least one arm of a frame, such as that used in Adson, Williams or McCulloch retractors. Such frames typically include two arms, but some frames have more than two arms. The arms of the frame are then moved apart to create a surgical workspace, with the at least one half-tube illuminator providing illumination of said space. One or more half-tube illuminators may also be provided with an extension that preferably is in contact with the opposite half tube and that serves to prevent tissue from filling in the gap created when the half tubes are separated. Tissue may enter this gap and interfere with surgery, so the extension helps reduce that issue.

Figure 35:
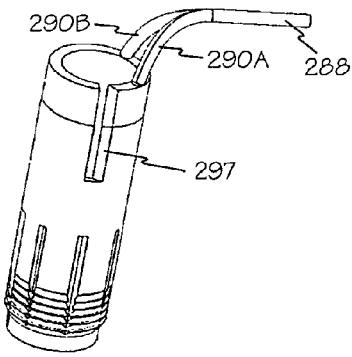
FIG. 35 is a perspective view of an alternate COP optical waveguide with a split input coupling.
Figure 36:
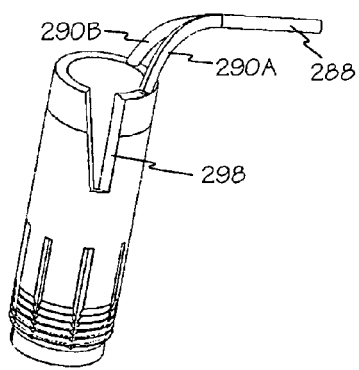
FIG. 36 is a perspective view of another alternate COP optical waveguide with a split input coupling.

FIGS. 35 and 36 illustrate alternative configurations of an illumination waveguide. Proximal reflecting structures such as proximal structure 297 and proximal structure 298 may provide more complete control of the light within the waveguide with an associated weakening of the structure.

Figure 37:
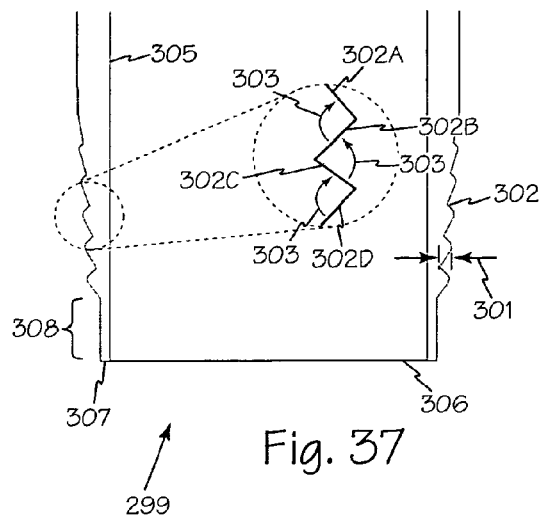
FIG. 37 is a cross section of the distal end of a COP optical waveguide.
Figure 38:
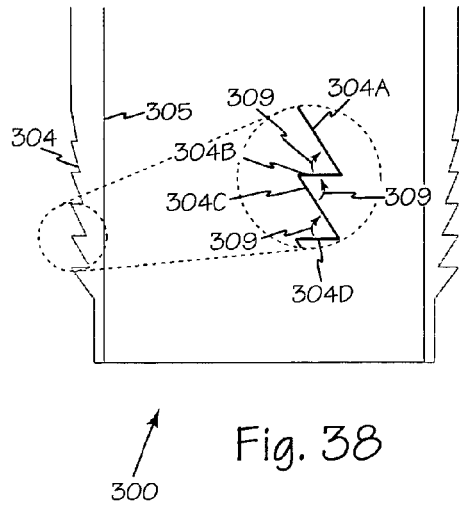
FIG. 38 is a cross-section of the distal end of an alternate COP optical waveguide.

Referring now to FIGS. 37 and 38, cross-sections 299 and 300 illustrate additional alternate light extraction structures of the distal end of an illumination waveguide. As shown with respect to FIG. 31 above, depth 301 of light extraction structures such as structures 302 and 304 increases relative to the distance from the light input in order to extract most of the light and send the light out the inner tube wall 305 toward the bottom or distal end 306 of the tube. The light that remains in the tube wall below the extraction structures exits the bottom edge 307, which may be flat or may have additional optical structures, e.g., a curved lens or a pattern of light diffusing structures such as structures 278 of FIG. 31. In FIG. 37, the distal 5-10 mm of the tube wall, window 308, have no structures to enable this surface to operate as a window to the surrounding tissues to improve visualization of the surgical space. As illustrated in FIG. 37, light extraction structures 302 are formed of adjacent facets such as facets 302A, 302B, 302C and 302D forming angles 303 between adjacent facets. In this illustration angles 303 are obtuse.

As illustrated in FIG. 38, light extraction structures 304 are formed of adjacent facets such as facets 304A, 304B, 304C and 304D forming angles 309 between adjacent facets. In this illustration angles 309 are acute. Any suitable angle may be used.

It has been demonstrated that a clear waveguide cannula provides improved visualization of the entire surgical workspace because the surgeon can see the layers of tissue through the walls, thereby enhancing the surgeon's sense of depth and position, which are difficult to determine in an opaque cannula. Light exiting the side walls at the areas of tissue contact, due to changes in total internal reflection at these contact areas, serves to illuminate these tissues making them more visible than if a non-illuminated, non-waveguide clear plastic cannula is used. Alternatively, extraction structures 302 or 304 may extend all the way down to bottom edge 307.

Referring now to FIGS. 39-42, light input connector 312C surrounds light input cylinder 312 which may be divided into multiple input arms such as arms 311 and 313 that then direct light into illumination waveguide 310. Input arms 311 and 313 may assume any suitable shape and cross-sections depending on the optical design goals, such as the multi-radius arms with rectangular cross-section shown or straight sections (no radius) or angle rotators, etc. Also shown is a clamp flange holder 314 that serves to support input connector 312C and arms as well as providing a standard light connector 312C over input cylinder 312 (e.g., an ACMI or WOLF connector) and a flange 314F at the top for attaching a clamp used to hold the entire structure in place once it is positioned relative to a surgical site in a body. A shelf or other similar light blocking structures may be added to the holder, extending over the input arms and or the upper tube edge as needed to help block any light that may escape these structures that might shine up into the user's eyes. Circumferential light extraction structures 316 are shown at the bottom, distal end 318, of the tube. In the section view of FIG. 40, vertical light disruption structures or facets 276F are shown on the inside wall of the tube.

Figure 39:
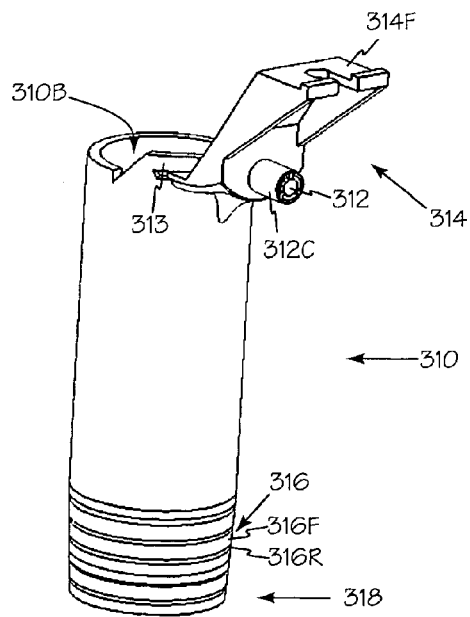
FIG. 39 is a perspective view of an alternate COP optical waveguide with a reinforced and shielded split input coupling.

Illuminated cannula 310 of FIG. 39 includes clamp adapter 314 that also support light coupling 312C for introducing light energy into cannula 310. The relative orientation of the clamp adapter and the light coupling as shown enables the clamp adapter to operate as a shield to prevent any misdirected light shining into the eyes of anyone looking into bore 310B of the cannula, but the clamp adapter and light coupling may adopt any suitable orientation.

Figure 40:
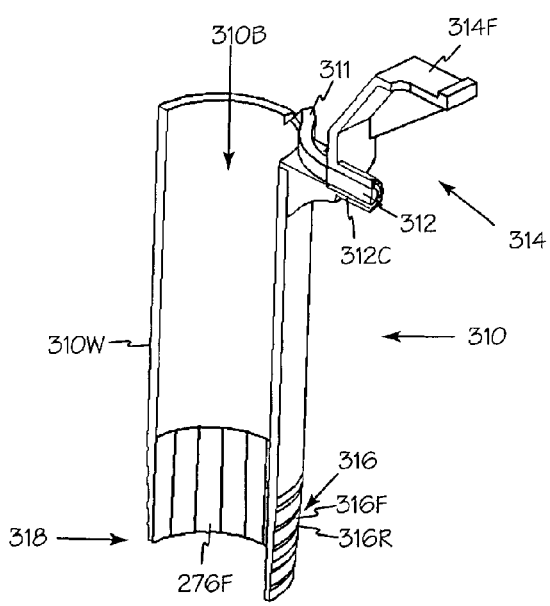
FIG. 40 is a cutaway view of the COP optical waveguide of FIG. 39.

FIG. 40 illustrates vertical facets 276F within the distal end for disrupting the light spiraling within the waveguide. Circumferential light extraction structures 316 may include stepped facets such as facets 316F and risers such as riser 316R on the outside tube wall 310W. The "riser" section of the stepped facet section 316R is angled so that it may slide against tissue without damaging the tissue. Steps may be uniform or non-uniform depending on the light directional control desired. The steps may be designed to direct light substantially inwards and toward the bottom of the tube or some distance from the bottom of the tube, or they may be designed to direct light toward the outside of the tube, or both.

Circumferential light extraction structures such as structures 316 may be facets or may be other geometries, such as parabolas. Circumferential light extraction structures coupled with light directing structures that provide circumferentially distributed light to the extraction structures provide circumferential illumination. Since tools entering the interior of the tube now have light shining on them from all sides, the tools do not cast any shadows within the cone of illumination emitted by the cannula. The circumferential illumination from a cylindrical waveguide creates a generally uniform cone of light that minimizes shadows, e.g., from instruments, creating substantially shadowless illumination in the surgical field below the tubular waveguide.

COP Cannula 310 of FIGS. 41 and 42 is illustrated without clamp flange/holder 314 in place. Input arms 311 and 313 above are offset above proximal surface 319 by a distance 320 and end in angled reflector surface 321 that partially extends down distance 322 into the tube wall. The offset controls the light entering waveguide 310 and restricts light entering to input structure 323. Reflector surface 321 serves to direct light orthogonally from the horizontal input and down into the tube wall, also causing the light to spread around the circumference of the tube wall by the time the light reaches the distal or lower part of the tube. Reflector surfaces such as surface 321 may be a flat surface, an arced surface, or a series of interconnected surfaces and may also end at the top of the tube wall. Reflector surface 321 may be treated, e.g., a reflective or metallized coating or an applied reflective film, to enhance reflection.

Air gaps may be used to isolate the light-conducting pathway in any suitable connector. Waveguide 310 of FIG. 43 includes male connector 324C that has been integrated with waveguide tube wall 310W via bracket 325. This allows connector 324C to be molded with the waveguide and not attached as a separate part, such as standard light connector 312C shown in FIG. 39. A separate connector introduces tolerance concerns into the system that may result in reduced coupling efficiency between a fiber optic cable output and waveguide input 326 because the two parts may not be aligned correctly. Molding the connector and the waveguide input as one piece substantially reduces the chance of misalignment and thereby increases coupling efficiency.

FIG. 44 is a front view looking into input 326 of connector 324C. Air gaps 327 are maintained around waveguide input 326 to isolate the light-conducting pathway. One or more small zones of contact such as contact zone 327C may be maintained, essentially bridging connector 324C and input 326 with a small amount of material, to add strength and stability to the system while resulting in minimum light loss in the contact zone.

COP Waveguide 330 of FIGS. 45 and 46 may be split open during surgery to permit greater access to the surgical field. Waveguide 330 is formed of cyclo olefin polymer. Light input channels 331 and 333 may be split and fed through a "Y". Waveguide 330 is fully split front and back from the top to about ½-⅔ of tube by slots 334 and 336. Alternatively, a waveguide may be split all the way to lower portion 330L. Lower portion 330L is scored inside and out with scoring such as score 337. The scoring operates to redirect light that may be trapped circling the tube. Bottom element 340 may also be a COP element and is pre-split in half along edge 341 and may be glued or otherwise secured in a waveguide such as COP waveguide 330. The generally planar shape of element 340 permits viewing through bottom element 340 and allows light to shine through. Alternatively, element 340 may also adopt any other suitable geometry such as rounded to form a lens. Because of the interface with the tube along edge 342 very little light is conducted into element 340. Hole 343 enables a surgical screw or other suitable connector to engage through bottom element 340 of waveguide 330 to a surgical site. Splitting waveguide 330 and bottom 340 frees the waveguide elements from a connector through hole 343, and permits the waveguide elements to be removed from the surgical site. While at least one light extraction structure is preferably located in lower portion 330L on each tube half, the at least one extraction structure may be located on only one half or may be located further up the tube, e.g., near the end of split 334 and or split 336.

Figure 47:
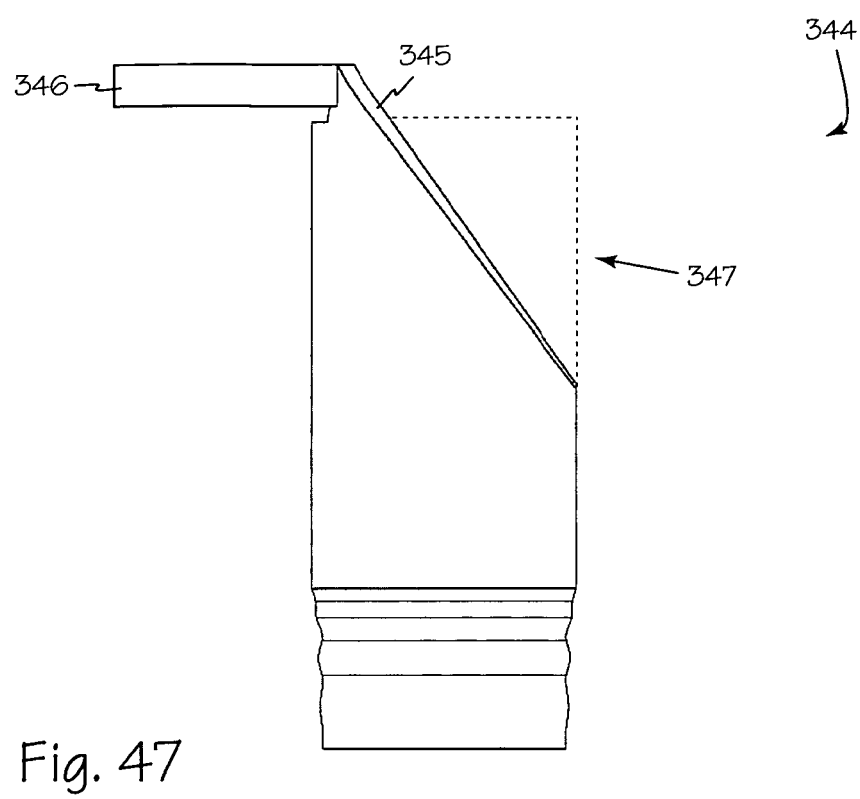
FIG. 47 is a cutaway view of a COP optical waveguide with an extended reflecting surface.

COP waveguide 344 in FIG. 47 has reflector face 345 extending down the side of waveguide 344 opposite light input 346, effectively removing material 347. Extended reflector face 345 serves to direct light circumferentially around the tube wall. This opens up the waveguide to provide improved access to the surgical space. In addition, it offers the opportunity to replace removed material 347 with more durable material to improve strength and or provide a second clamp flange holder and or to provide mounting for other devices, such as a CCD camera.

Illuminated COP retractors such as cannula, waveguides, tubes and or sheaths may also benefit from extendable skirts or segments to prevent tissue encroaching on a surgical site. The extendable elements may also include interface surfaces to introduce light into the elements to enhance surgical site illumination and or provide off axis illumination to enhance shadows for better depth perception and tissue discrimination.

The illuminated COP retractors as discussed above may also be made extendable or telescoping to enable a varying depths of surgery with a single thus device minimizing hospital inventory. The illuminating cannulas discussed may also be formed as an illuminating drill guide, either as a tube or as two half tubes, that may be used to hold and guide drill or burr tip while also providing illumination of the area being worked on.

A COP illuminator may be characterized as having a light input portion, a light conducting portion and a light output portion. The light input portion of the COP illuminator receives light from an external light source. Such a light source may be an external light box, e.g., a xenon light box, to which one end of a fiber optic light guide cable is attached to conduct light to the surgical field. In this instance, the other end of the fiber optic cable would be the source of light for the blade insert illuminator, for example, by employing a mating connector on the illuminator so that it may connect to the fiber optic cable. The light input portion may also include a tab, finger or other projection extending from a dead zone to engage the retractor blade at the top or handle end, the projection may be permanently integrated or temporarily attached.

The light conducting portion of the COP illuminator typically is responsible for conducting light from the light input section to the light output section. It may be simply a section of optical material designed to support total internal reflection that is integral with the light input and light output portions. Surface treatment, e.g., polishing or reflective coating, and the continuous air gap may be used to support total internal reflection.

The light output portion of the COP illuminator may contain any suitable number of output zones of generally similar depth, each zone having specially designed output optical structures that control and direct light to escape the illuminator to shine onto a predetermined area of interest or to have a predetermined shape or footprint. Such structures may be molded or cut into the light output zones. In some configurations, two to eight output zones are provided.

A cyclo olefin polymer air gap retractor illumination system includes any suitable retractor such as a McCulloch with a channel in the blade to accommodate an air gap illuminator. The COP illuminator has active portions in which light passes and inactive or dead zones in which light does not pass as a result of the configuration and orientation of the input, output and surfaces of the illuminator. The illuminator is formed to have an air gap surrounding any active portion of the illuminator extending from the light input to the light output portion. The dead zones may include elements to allow the illuminator to securely engage the retractor. The light output portion of the illuminator may contain any suitable number of output zones, each zone having specially designed output optical structures that control and direct light to escape the illuminator to shine onto a predetermined area of interest or to form one or more predetermined shapes or footprints.

A COP blade insert illuminator may comprise one or more illuminator sections designed to engage a mating channel or channels formed in the blade. Blade insert illuminators may be characterized by having a light input portion, a light conducting portion and a light output portion. The blade illuminator may be oriented at any suitable position along the retractor blade channel. A COP blade illuminator may be adapted to temporarily or permanently attach to any other suitable surgical instrument such as for example, a Gelpi retractor.

The light input portion of a COP blade insert illuminator receives light from an external light source. Such a light source may be an external light box, e.g., a xenon light box, to which one end of a fiber optic light guide cable is attached to conduct light to the surgical field. In this instance, the other end of the fiber optic cable would be the source of light for the blade insert illuminator, for example, by employing a mating connector on the illuminator so that it may connect to the fiber optic cable. The light input portion may include a short section of a light conducting material, such as for example, a suitable plastic or a fiber optic bundle, that is permanently integrated or temporarily attached.

The light conducting portion of a COP blade insert illuminator typically is responsible for conducting light from the light input section to the light output section. It may be simply a section of optical material designed to support total internal reflection that is integral with the light input and light output portions. Any suitable surface treatment, such as for example, polishing, reflective coating, anti-reflective (AR) coatings and or dielectric coatings may be used to support total internal reflection.

The light output portion of a COP blade insert illuminator contains specially designed output optical structures that allow light to be extracted from the illuminator to shine onto a predetermined area of interest. Such structures may be molded into the light output portion or such structures may be applied, for example, as a film.

A COP blade insert illumination system may consist of a single illuminator that contains the light input, light conducting and light output portions in a simple, single device that acts as a waveguide. Such a system may also be comprised of different sections of illuminator components that attach together to form a complete system. In this case, there may be a light input section designed to receive light from a light source, one or more light conduit sections designed to conduct light from the light input section to a light output section, and a light output section containing the optical output structures that allow light to escape and illuminate a predetermined area of interest, said sections attaching together to form a complete system. Each section acts as a waveguide and may employ optical structures to polarize and or filter the light energy entering or exiting the waveguide.

A COP blade insert illuminator must be designed and fabricated to maximize light transfer from the light source or fiber optic input cable and minimize light loss from the waveguide in order to provide an efficient light transmission system. Efficiency is particularly important for LED and other light sources, e.g., halogen or xenon lamps, because it directly determines the required brightness of the LED. An inefficient waveguide experiences significant light loss, typically 60% of light may be lost from input to output. Such a light guide would require a high power LED to provide sufficient light. A high power LED requires a lot of power and generates significant heat, thereby requiring large batteries and bulky and inconvenient heat sinking devices and methods that add to the size and increase the difficulty of using such a device. Other high power light sources often require noisy fans, which may disturb the medical personnel conducting a surgery or medical exam. Lamps used in high power light sources have a limited life time, requiring frequent and expensive replacement, due to the need to drive the lamp at high power levels to generate enough light. An efficient waveguide, one in which light loss is typically less than 30%, allows a much lower power LED or other light source to be used, thereby significantly reducing or eliminating the need for special heat sinking devices and methods, reducing cost, and improving the usability of the device. The design of an efficient blade insert illumination waveguide may involve special design of the light input portion of the waveguide to efficiently capture the incoming light, for example, by careful selection of numerical apertures or using a lens, design and fabrication of the light reflecting walls of the light conducting portion of the waveguide to maintain surface finish to maximize reflection and reduce light lost through refraction, the use of reflective or dampening coatings, the design of light directing optical structures that direct the light toward the light output optical structures while minimizing light loss through refraction, and or the design of light output optical structures that maximize light exiting the waveguide through refraction, particularly refraction of light in certain directions, while minimizing light lost through reflection.

While the preferred embodiments of the devices and methods have been described in reference to the environment in which they were developed, they are merely illustrative of the principles of the inventions. Other embodiments and configurations may be devised without departing from the spirit of the inventions and the scope of the appended claims. Additionally, while the above is a complete description of the preferred embodiments of the invention, various alternatives, modifications, and equivalents may be used. For example, many of the optical components are disclosed as being formed from COP. One of skill in the art will appreciate that COC may also be used to form those components. Therefore, the above description should not be taken as limiting the scope of the invention which is defined by the appended claims.

What is claimed is:

1. An illuminated medical system comprising:
   a medical instrument; and
   a light transmitting waveguide having an inner surface, an outer surface, a proximal region and a distal region, the waveguide coupled to the medical instrument, wherein the waveguide is configured to conduct light from the proximal region to the distal region thereof, and the waveguide projects the light from the distal region toward a target area, and
   wherein the waveguide comprises a plurality of zones on the inner surface or on the outer surface, and a plurality of facets disposed in each of the plurality of zones, the plurality of facets in a first zone having a different shape than the plurality of facets in a second zone, the plurality of facets extracting the light from the waveguide and directing the extracted light to a surgical field, and wherein the plurality of facets are integrally formed with the waveguide, and
   wherein the waveguide is rigid and consists essentially of a cyclic olefin copolymer or a cyclic olefin polymer.

2. The system of claim 1, wherein the medical instrument comprises one of a surgical retractor, a laryngoscope, a speculum, or an anoscope.

3. The system of claim 1, wherein the waveguide is adjustably positionable relative to the medical instrument thereby allowing adjustment of the projected light onto the target area.

4. The system of claim 1, wherein the waveguide further comprises one or more output optical structures disposed adjacent the distal region thereof, the output optical structures configured to direct the light from the distal region of the waveguide to the target area.

5. The system of claim 4, wherein the output optical structures comprise one or more facets.

6. The system of claim 1, wherein the waveguide comprises a tubular body.

7. The system of claim 1, wherein the waveguide comprises an elongate blade.

8. The system of claim 1, wherein the waveguide comprises a half tubular body.

9. The system of claim 1, further comprising:
   an illumination source that provides the light;
   an illumination conduit optically coupled with the illumination source and the waveguide, the illumination conduit configured to conduct light from the illumination source to the waveguide; and
   an optical coupling coupled to the waveguide and the illumination conduit, the optical coupling configured to optically couple the illumination conduit with the waveguide so that the light may pass therebetween, and wherein the optical coupling also releasably holds the illumination conduit and the waveguide together.

10. The system of claim 1, wherein the waveguide has a specific gravity less than polycarbonate or acrylic.

11. The system of claim 1, wherein the waveguide has a water absorption rate less than polycarbonate or acrylic.

12. The system of claim 11, wherein the water absorption rate of the waveguide is less than 0.01%.

13. The system of claim 1, wherein the waveguide transmits light with greater efficiency than polycarbonate or with efficiency greater than or equal to acrylic.

14. The system of claim 13, wherein the light transmittance of the waveguide is 90% or greater.

15. The system of claim 1, wherein the waveguide has a refractive index greater than acrylic.

16. The system of claim 15, wherein the refractive index of the waveguide is greater than 1.49.

17. The system of claim 1, wherein the waveguide has a glass transition temperature higher than that of polycarbonate.

18. The system of claim 17, wherein the glass transition temperature of the waveguide is greater than or equal to 105° C.

19. The system of claim 1, wherein the waveguide is biocompatible.

20. An illuminated medical system comprising:
   a medical instrument; and
   a rigid light transmitting illuminator having an inner surface, an outer surface, a proximal region and a distal region, the illuminator coupled to the medical instrument,
   wherein the illuminator is configured to conduct light from the proximal region to the distal region thereof, and the illuminator comprises a light input portion, a light conducting portion, and a light output portion,
   wherein the light output portion comprises a plurality of zones on the inner surface or on the outer surface, and a plurality of facets disposed in each of the plurality of zones, the plurality of facets in a first zone having a different shape than the plurality of facets in a second zone, the plurality of facets extracting the light from the waveguide and directing the extracted light to a target area, and wherein the plurality of facets are integrally formed with the illuminator,
   wherein the light output portion projects the light from the distal region of the illuminator towards the target area, and
   wherein the light conducting portion consists essentially of a cyclic olefin copolymer or a cyclic olefin polymer.

21. The system of claim 20, wherein the medical instrument comprises one of a surgical retractor, laryngoscope, a speculum, or an anoscope.

22. The system of claim 20, the light output portion is adjustably positionable relative to the medical instrument thereby allowing adjustment of the projected light onto the target area.

23. The system of claim 20, wherein the light output portion comprises one or more output optical structures disposed adjacent the distal region thereof, the output optical structures configured to direct the light from the light output portion to the target area.

24. The system of claim 23, wherein the output optical structures comprise one or more facets.

25. The system of claim 20, wherein the light conducting portion comprises a tubular body.

26. The system of claim 20, wherein the light conducting portion comprises an elongate blade.

27. The system of claim 20, wherein the light conducting portion comprises a half tubular body.

28. The system of claim 20, further comprising:
an illumination source that provides the light; and
an illumination conduit optically coupled with the light input portion and the illumination source, the illumination conduit configured to conduct light from the illumination source to the light input portion.

29. A method for illuminating a medical work space, said method comprising:
providing a medical instrument coupled to a light transmitting waveguide, the waveguide having an inner surface and an outer surface;
advancing the medical instrument and the waveguide toward the work space;
illuminating the work space with light from at least one of the inner and outer surfaces of the waveguide, wherein the waveguide comprises a plurality of zones on the inner surface or on the outer surface, and a plurality of facets disposed in each of the plurality of zones, the plurality of facets in a first zone having a different shape than the plurality of facets in a second zone, the plurality of facets extracting the light from the waveguide and directing the extracted light to the medical work space, and wherein the plurality of facets are integrally formed with the waveguide, and wherein the light passes from a proximal portion of the waveguide to a distal portion of the waveguide, and wherein the waveguide is rigid and consists essentially of a cyclic olefin copolymer or a cyclic olefin polymer.

30. The method of claim 29, wherein the medical instrument comprises one of a surgical retractor, a laryngoscope, a speculum, or an anoscope.

31. The method of claim 29, wherein advancing the medical instrument and the waveguide further comprises positioning the medical instrument in a patient and retracting tissue.

32. The method of claim 29, wherein advancing the medical instrument and the waveguide comprises positioning the medical instrument and the waveguide in a body orifice.

33. The method of claim 29, wherein advancing the medical instrument and the waveguide comprises positioning the medical instrument and the waveguide into an incision.

34. The method of claim 29, wherein the waveguide comprises a tubular body having a central channel, and advancing the medical instrument comprises positioning the medical instrument through the central channel.

35. The method of claim 29, wherein illuminating comprises adjusting waveguide position relative to the medical instrument, thereby adjusting illumination of the work space.

36. The method of claim 29, wherein illuminating comprises optically coupling the waveguide with an illumination source.

37. The system of claim 1, wherein the waveguide has a cross-section, and the cross-section changes from the proximal region to the distal region.

38. The system of claim 20, wherein the illuminator has a cross-section, and the cross-section changes from the proximal region to the distal region.

39. The method of claim 29, wherein the waveguide has a cross-section, and the cross-section changes from the proximal portion to the distal portion.

* * * * *